(12) United States Patent
Amano

(10) Patent No.: US 6,592,528 B2
(45) Date of Patent: Jul. 15, 2003

(54) BIOLOGICAL INFORMATION EVALUATION APPARATUS

(75) Inventor: Kazuhiko Amano, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 75 days.

(21) Appl. No.: 09/815,645

(22) Filed: Mar. 23, 2001

(65) Prior Publication Data
US 2002/0072860 A1 Jun. 13, 2002

(30) Foreign Application Priority Data

Mar. 23, 2000 (JP) .................................... 2000-081558
Jul. 7, 2000 (JP) .................................... 2000-206711
Nov. 22, 2000 (JP) .................................... 2000-355930

(51) Int. Cl.$^7$ ................................................ A61B 5/00
(52) U.S. Cl. .......................... 600/485; 600/500; 600/587
(58) Field of Search ................................ 600/485, 490, 600/493–6, 500–505, 587

(56) References Cited

U.S. PATENT DOCUMENTS

| | | | |
|---|---|---|---|
| 5,000,188 A | | 3/1991 | Kojima |
| 5,582,179 A | * | 12/1996 | Shimizu et al. ............. 600/500 |
| 5,623,933 A | * | 4/1997 | Amano et al. ............. 600/500 |
| 5,649,536 A | | 7/1997 | Ogura et al. |
| 5,671,750 A | * | 9/1997 | Shinoda ..................... 600/500 |
| 5,715,826 A | * | 2/1998 | Horrocks et al. ........... 600/485 |
| 5,853,371 A | * | 12/1998 | Inukai et al. ............... 600/485 |
| 5,961,467 A | * | 10/1999 | Shimazu et al. ............. 600/500 |
| 6,309,359 B1 | * | 10/2001 | Whitt et al. ................ 600/485 |
| 6,338,719 B1 | * | 1/2002 | Drzewiecki et al. ........ 600/485 |

FOREIGN PATENT DOCUMENTS

| | | |
|---|---|---|
| JP | 59-91389 | 5/1984 |
| JP | 61-119252 | 6/1986 |
| JP | 3-15439 | 1/1991 |
| JP | 7-95966 | 4/1995 |
| JP | 7-284480 | 10/1995 |
| JP | 11-104089 | 4/1999 |
| JP | 2000-51166 | 2/2000 |
| WO | WO99/26529 | 6/1999 |

* cited by examiner

Primary Examiner—Robert L. Nasser
(74) Attorney, Agent, or Firm—Mark P. Watson

(57) ABSTRACT

A biological information evaluation apparatus includes a waveform parameter detection section, a corresponding relation storage section, and a blood vessel evaluation information deriving section. The waveform parameter detection section detects a waveform parameter such as an after-ejection pressure ratio or dicrotic wave height ratio based on a pulse waveform. The corresponding relation storage section stores the corresponding relation between the blood vessel evaluation information and the waveform parameter which is derived in advance. The blood vessel evaluation information deriving section derives the blood vessel evaluation information based on the waveform parameter detected by the waveform parameter detection section and the corresponding relation. The waveform parameter detection section includes a pulse wave sensor which detects the pulse waveform, and a waveform parameter calculation section which calculates the waveform parameter from the pulse waveform.

27 Claims, 19 Drawing Sheets

BIOLOGICAL INFORMATION EVALUATION APPARATUS

Japanese Patent Application No. 2000-81558 filed Mar. 23, 2000, Japanese Patent Application No. 2000-206711 filed Jul. 7, 2000, and Japanese Patent Application No. 2000-355930 filed Nov. 22, 2000 are hereby incorporated by reference in their entirety.

TECHNICAL FIELD

The present invention relates to a biological information evaluation apparatus which derives blood vessel evaluation information based on a pulse waveform.

BACKGROUND ART

As a method for evaluating the physiological age of blood vessels which relates to the degree of arteriosclerosis and the like, an invasive method such as measurement of cholesterol or fat in blood, and a noninvasive method utilizing biological imaging techniques such as ultrasonic tomography, positron emission tomography (PET), or magnetic resonance imaging (MRI) are known.

However, invasive methods cannot be easily carried out at any time. Methods based on biological imaging technique are noninvasive, but require large-scale apparatus. Therefore, these methods cannot also be easily carried out at any time.

A known physical fact is that the pulse wave velocity in the arteries increases as the hardening of the blood vessels progresses. As a noninvasive method utilizing this fact, there is a method of judging the degree of arteriosclerosis of the aorta by measuring the pulse wave velocity, thereby estimating the arterial elasticity. However, it is considered difficult to quantitatively measure the degree of arteriosclerosis by this method with good reproducibility due to effects of the autonomous nervous system on the peripheral arterial system.

Therefore, an apparatus using an arterial pulse waveform has been proposed as a noninvasive apparatus with good reproducibility which is capable of easily evaluating the physiological age or degree of arteriosclerosis of blood vessels.

For example, Japanese Patent Application Laid-open No. 61-119252 discloses an arteriosclerosis measuring apparatus. This apparatus stores in advance a plurality of pulse wave standard patterns corresponding to the stages of hardening of the arteries. The degree of arteriosclerosis is evaluated by determining that the pulse wave detected in the artery of the living body has the greater correlation coefficient with which standard pattern.

Japanese Patent Application Laid-open No. 3-15439 discloses a physiological age measuring apparatus in which a standard pattern close to the pulse wave obtained by a pulse wave sensor pressed against the artery is selected by comparing the pulse wave with a plurality of pulse wave standard patterns which differ according to the age of the living body. The physiological age of the living body is determined based on the selected standard pattern.

These apparatuses select the standard pattern close to the measured pulse wave by calculating the correlation coefficient for the pulse wave standard patterns and the measured pulse wave. The degree of arteriosclerosis or physiological age of the living body whose pulse wave has been measured is estimated based on the degree of arteriosclerosis or physiological age corresponding to the selected standard pattern. Therefore, these apparatuses require a large capacity memory for storing a number of standard patterns. Moreover, a large number of arithmetic operations are needed for calculating the correlation coefficient between a number of standard patterns and the measured pulse wave. Therefore, it is difficult to create an apparatus small enough to be portable.

The present inventor disclose a pulse waveform monitoring apparatus for monitoring the pulse waveform and a pharmacological action monitoring apparatus for monitoring the pharmacological action based on indexing using the difference in levels between characteristic portions of the pulse waveform in International Patent Application No. PCT/JP98/05259. However, an apparatus for evaluating the physiological age or degree of arteriosclerosis of blood vessels is not disclosed in that application.

SUMMARY OF THE INVENTION

A first aspect of the present invention provides a biological information evaluation apparatus comprising:

a waveform parameter detection section which detects a specific waveform parameter based on a pulse waveform;

a corresponding relation storage section which stores the corresponding relation between blood vessel evaluation information and the waveform parameter which is derived in advance; and a blood vessel evaluation information deriving section which derives the blood vessel evaluation information based on the waveform parameter detected by the waveform parameter detection section and the corresponding relation.

The biological information evaluation apparatus stores in advance the corresponding relation between a specific waveform parameter in the pulse waveform and the blood vessel evaluation information in the corresponding relation storage section. The blood vessel evaluation information deriving section uniquely derives the blood vessel evaluation information by applying the detected waveform parameter to the corresponding relation. Therefore, the blood vessel evaluation information can be derived without the need for a large memory capacity or a large number of arithmetic operations. Note that the blood vessel evaluation information reflects changes in organic physical property as tissue and dynamic and functional changes accompanied by the activities of the autonomous nervous system.

Another aspect of the present invention provides a biological information evaluation apparatus comprising:

a waveform parameter detection section which detects a specific waveform parameter based on a blood pressure waveform;

a corresponding relation storage section which stores the corresponding relation between blood vessel evaluation information and the waveform parameter which is derived in advance; and a blood vessel evaluation information deriving section which derives the blood vessel evaluation information based on the waveform parameter detected by the waveform parameter detection section and the corresponding relation.

The biological information evaluation apparatus according to the present embodiment stores in advance the corresponding relation between a specific waveform parameter in the blood pressure waveform and the blood vessel evaluation information in the corresponding relation storage section. The blood vessel evaluation information deriving section uniquely derives the blood vessel evaluation information by applying the detected waveform parameter to the corresponding relation. Therefore, the blood vessel evaluation information can be derived without the need for a large memory capacity or a large number of arithmetic operations.

DETAILED DESCRIPTION OF THE EMBODIMENTS

1. Basic Principle

The basic principle in each embodiment of the present invention is based on the following facts confirmed by the inventor.

Figure 1:
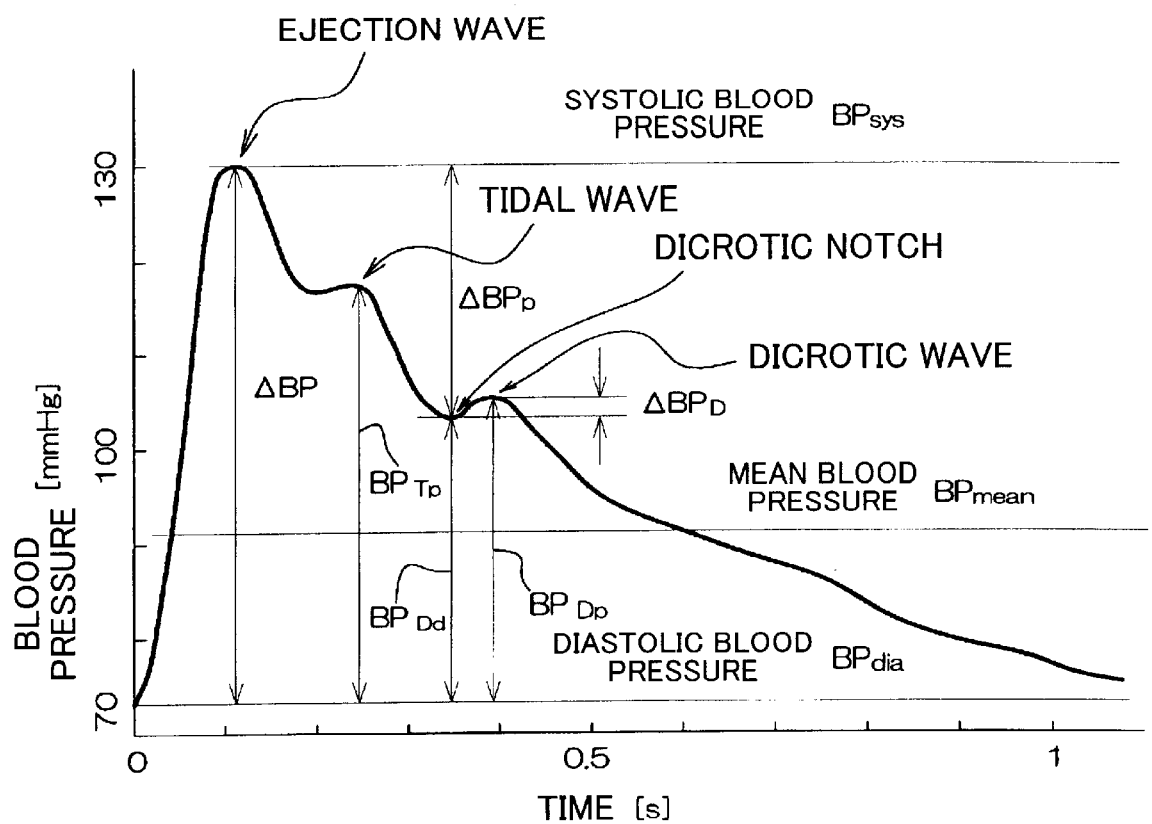
FIG. 1 is a graph showing a typical blood pressure waveform in an artery.

FIG. 1 is a graph showing a typical blood pressure waveform in an artery such as the radial artery. As shown in FIG. 1, the blood pressure waveform in an artery generally has an ejection wave having the highest peak, a tidal wave having the second highest peak, and a dicrotic wave having a third peak. A minimum point or an inflection point between the tidal wave and the dicrotic wave is called a dicrotic notch. The peak of the ejection wave corresponds to a systolic blood pressure (maximum blood pressure) $BP_{sys}$ which is the highest blood pressure in the blood pressure waveform. A diastolic blood pressure (minimum blood pressure) $BP_{dia}$ corresponds to the lowest blood pressure in the blood pressure waveform. The pressure difference between the systolic blood pressure $BP_{sys}$ and the diastolic blood pressure $BP_{dia}$ is called a pulse pressure $\Delta BP$. A mean blood pressure $BP_{mean}$ is obtained by integrating the blood pressure waveform and calculating the time average of the resulting value.

In the present specification, the pressure difference between the systolic blood pressure $BP_{sys}$ and the blood pressure at the dicrotic notch is called an after-ejection pressure $\Delta BP_P$, and the pressure difference between the blood pressure at the dicrotic notch and the blood pressure at the dicrotic wave peak is called a dicrotic wave height $\Delta BP_D$.

Figure 2:
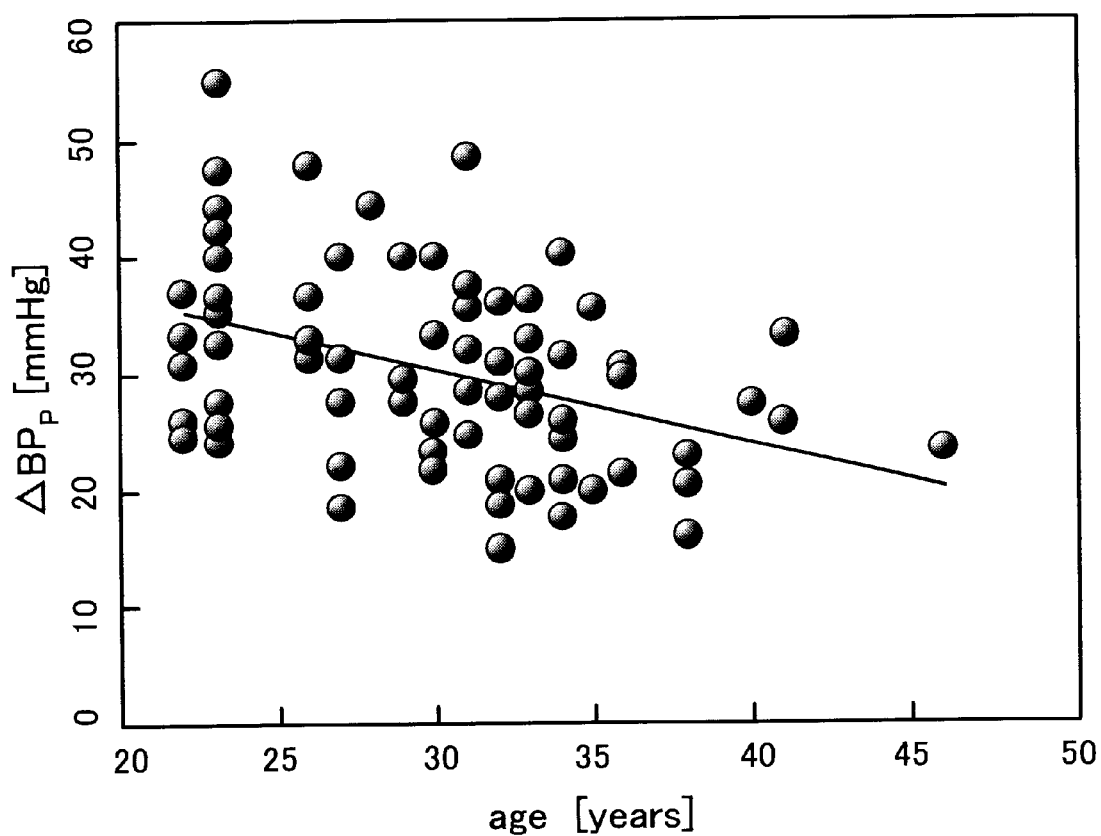
FIG. 2 is a graph in which measurement data for after-ejection pressure is plotted relative to the ages of subjects.
Figure 3:
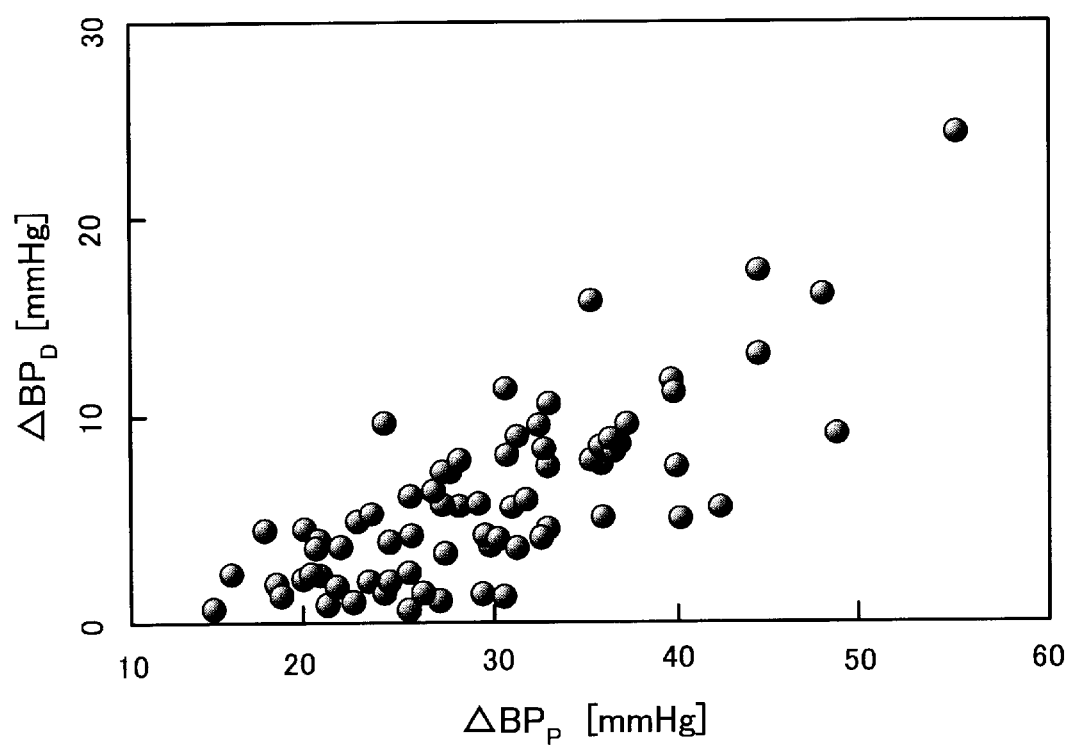
FIG. 3 is a graph in which measurement data for after-ejection pressure and dicrotic notch height is plotted.

The present inventor measured the blood pressure waveform in the radial artery of eighty healthy adults ranging from twenty two to forty six years of age, who were seated after resting for 15 minutes while they were hungry (09:30 to 13:30). FIGS. 2 and 3 are graphs showing the results plotted for data obtained by the measurement.

Specifically, FIG. 2 clearly shows that there is a tendency for a linear functional relationship (correlation coefficient r=−0.41) or a monotone functional relationship between the after-ejection pressure $\Delta BP_P$ and the subject's age. Therefore, a relational equation was determined based on the data shown in FIG. 2 on the assumption that there was a linear functional relationship between the after-ejection pressure $\Delta BP_P$ and the subject's age. If the subject's age (years) is x and the after-ejection pressure $\Delta BP_P$ (mmHg) is y, the relational equation is expressed as follows.

$$y=-0.62x+48.8 \quad (1)$$

Note that this equation is based on the data shown in FIG. 2. A more ideal relational equation is expected to be obtained by using data covering broader age groups and population.

FIG. 3 shows that there is a strong linear functional relationship (correlation coefficient r=0.77) between the after-ejection pressure $\Delta BP_P$ and the dicrotic wave height $\Delta BP_D$.

Therefore, the physiological age can be estimated by the after-ejection pressure $\Delta BP_P$ or dicrotic wave height $\Delta BP_D$. It is known that the degree of arteriosclerosis generally progresses as age increases. Therefore, the degree of arteriosclerosis can be estimated by the after-ejection pressure $\Delta BP_P$ or dicrotic wave height $\Delta BP_D$.

Nifedipine, which is a calcium channel blocker having a vasodilator effect, exhibits a pharmacological action for temporarily improving distensibility of the blood vessel. This action is considered to be an action for temporarily decreasing the physiological age (degree of arteriosclerosis) of the blood vessels. The present inventor have estimated the physiological age of the blood vessels of six subjects before and after the administration of nifedipine using the relation represented by the above equation (1) by measuring the after-ejection pressure $\Delta BP_P$ (mmHg) before and after the administration of nifedipine. The results are shown in Table 1. In Table 1, the physiological age before administration is the physiological age of the blood vessels estimated from the after-ejection pressure $\Delta BP_P$ obtained from the average of the radial artery pressure waveforms one hour before the administration of nifedipine. The physiological age after administration is the physiological age of the blood vessels estimated from the after-ejection pressure $\Delta BP_P$ obtained from the average of the radial artery pressure waveform one hour after the administration of nifedipine.

TABLE 1

|  | Age | Physiological age before administration | Physiological age after administration |
| --- | --- | --- | --- |
| A | 29 | 28 ± 4 | 29 ± 2 |
| B | 23 | 23 ± 3 | 21 ± 4 |
| C | 35 | 30 ± 2 | 21 ± 4 |
| D | 23 | 28 ± 1 | 22 ± 2 |
| E | 41 | 34 ± 2 | 30 ± 1 |
| F | 30 | 35 ± 1 | 27 ± 4 |

As shown in Table 1, although a significant difference in the estimated physiological age was not observed for the subjects A and B before and after the administration of nifedipine, the physiological age was significantly decreased for four subjects C to F after the administration of nifedipine. As described above, estimation of the physiological age (degree of arteriosclerosis) of the blood vessels using a linear functional relationship between the after-ejection pressure $\Delta BP_P$ and the physiological age of the blood vessels showed results which coincide with the pharmacological action of nifedipine.

Figure 4:
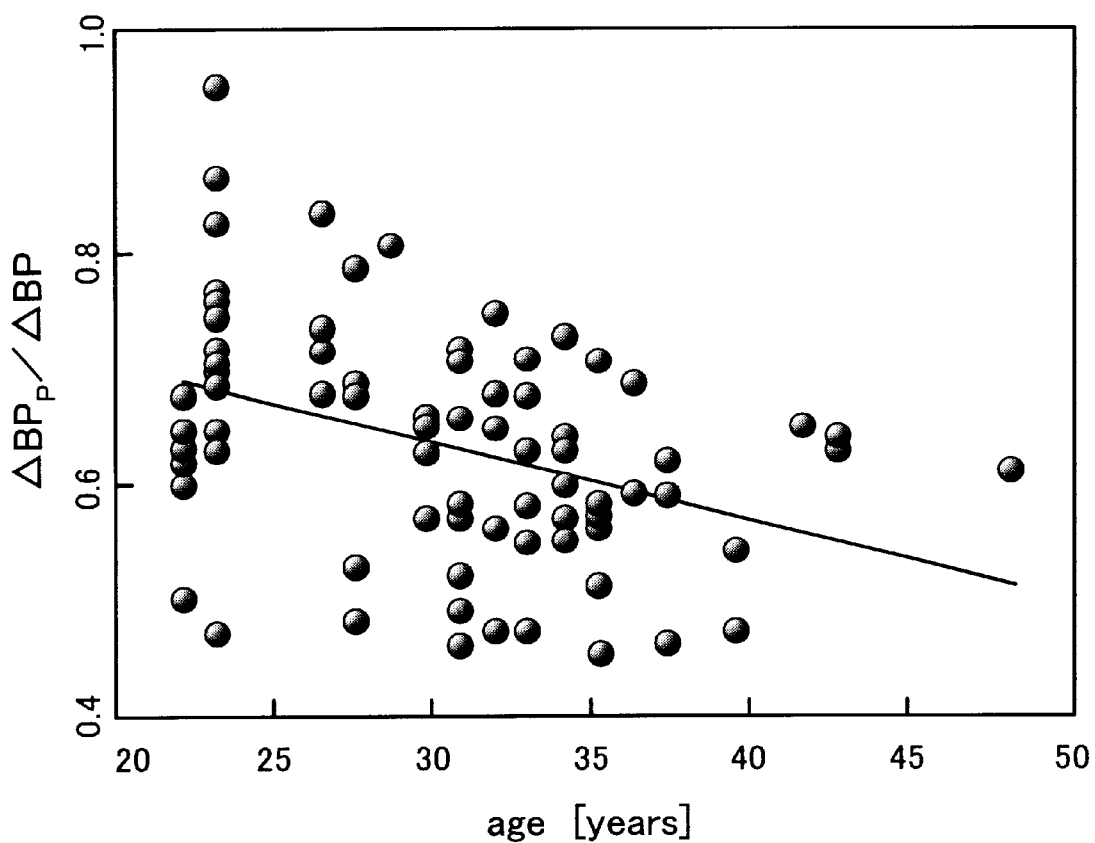
FIG. 4 is a graph in which an after-ejection pressure ratio is plotted relative to the ages of subjects.

An after-ejection pressure ratio $\Delta BP_P/\Delta BP$ which is the after-ejection pressure $\Delta BP_P$ normalized by the pulse pressure $\Delta BP$ may be used in place of the after-ejection pressure $\Delta BP_P$. A dicrotic wave height ratio $\Delta BP_D/\Delta BP$ which is the dicrotic wave height $\Delta BP_D$ normalized by the pulse pressure $\Delta BP$ may be used in place of the dicrotic wave height $\Delta BP_D$. The relation between the after-ejection pressure ratio $\Delta BP_P/\Delta BP$ and the subjects' age under the same conditions as described above is plotted on a graph shown in FIG. 4. As is clear from FIG. 4, there is a linear functional relationship (correlation coefficient r=−0.39) or a monotone functional relationship between the after-ejection pressure ratio $\Delta BP_P/\Delta BP$ and the subject's age. Therefore, the physiological age or degree of arteriosclerosis can be estimated by the after-ejection pressure ratio $\Delta BP_P/\Delta BP$. The physiological age or the degree of arteriosclerosis can also be estimated by the dicrotic wave height ratio $\Delta BP_D/\Delta BP$.

2. Overview of Embodiments
2.1 One embodiment of the Present Invention

One embodiment of the present invention provides a biological information evaluation apparatus comprising:

a waveform parameter detection section which detects a specific waveform parameter based on a pulse waveform;

a corresponding relation storage section which stores the corresponding relation between blood vessel evaluation information and the waveform parameter which is derived in advance; and a blood vessel evaluation information deriving section which derives the blood vessel evaluation information based on the waveform parameter detected by the waveform parameter detection section and the corresponding relation.

In this embodiment, the corresponding relation between a specific waveform parameter in the blood pressure waveform and the blood vessel evaluation information in the corresponding relation storage section is stored in advance. The blood vessel evaluation information deriving section uniquely derives the blood vessel evaluation information by applying the detected waveform parameter to the corresponding relation. Therefore, the blood vessel evaluation information can be derived without the need for a large memory capacity or a large number of arithmetic operations. Note that the blood vessel evaluation information reflects changes in organic physical property as tissue and dynamic and functional changes accompanied by the activities of the autonomous nervous system.

The biological information evaluation apparatus according to the present embodiment may further include any of the following features.

(1) The waveform parameter detection section may include a pulse wave sensor which detects the pulse waveform, and a waveform parameter calculation section which calculates the waveform parameter from the pulse waveform.

This enables the waveform parameter to be calculated from the pulse waveform detected by the pulse wave sensor.

(2) The waveform parameter may be an after-ejection pressure ratio that is an after-ejection pressure normalized by a pulse pressure, the after-ejection pressure being pressure difference between a blood pressure at a dicrotic notch and a maximum pressure, and the pulse pressure being pressure difference between the maximum blood pressure and a minimum blood pressure.

This enables the blood vessel evaluation information to be obtained by the after-ejection pressure ratio obtained from the pulse wave form based on the fact, confirmed by the inventor, that the after-ejection pressure ratio and age have a linear functional relationship or monotone functional relationship with high probability.

(3) The waveform parameter may be a dicrotic wave height ratio which is a dicrotic wave height normalized by a pulse pressure, the dicrotic wave height being pressure difference between a blood pressure at a dicrotic notch and a blood pressure at a dicrotic wave peak, and pulse pressure being pressure difference between a maximum blood pressure and a minimum blood pressure.

This enables the blood vessel evaluation information to be obtained by the dicrotic wave height ratio obtained from the pulse waveform based on the fact, confirmed by the inventor, that the after-ejection pressure ratio, which has a linear functional relationship or monotone functional relationship with age with high probability, and the dicrotic wave height ratio have a linear functional relationship.

2.2 Another Embodiment of the Present Invention

Another embodiment of the present invention provides a biological information evaluation apparatus comprising:

a waveform parameter detection section which detects a specific waveform parameter based on a blood pressure waveform;

a corresponding relation storage section which stores the corresponding relation between blood vessel evaluation information and the waveform parameter which is derived in advance; and a blood vessel evaluation information deriving section which derives the blood vessel evaluation information based on the waveform parameter detected by the waveform parameter detection section and the corresponding relation.

In this embodiment, the corresponding relation between a specific waveform parameter in the pulse waveform and the blood vessel evaluation information in the corresponding relation storage section is stored inadvance. The blood vessel evaluation information deriving section uniquely derives the blood vessel evaluation information by applying the detected waveform parameter to the corresponding relation. Therefore, the blood vessel evaluation information can be derived without the need for a large memory capacity or a large number of arithmetic operations.

The biological information evaluation apparatus according to the present embodiment may further include any of the following features.

(1) The waveform parameter detection section may include a blood pressure measurement section which detects a maximum blood pressure and a minimum blood pressure, a pulse wave sensor which detects a pulse waveform, a conversion section which converts the pulse waveform into a blood pressure waveform, and a waveform parameter calculation section which calculates the waveform parameter from the blood pressure waveform.

This allows the conversion section to convert the pulse waveform detected by the pulse wave sensor into the blood pressure waveform using the maximum blood pressure and minimum blood pressure measured by the blood pressure measurement section. This enables the waveform parameter calculation section to calculate the waveform parameter based on the blood pressure waveform.

(2) The waveform parameter may be an after-ejection pressure which is pressure difference between a blood pressure at a dicrotic notch and a maximum blood pressure.

This enables the blood vessel evaluation information to be obtained by the after-ejection pressure obtained from the blood pressure waveform based on the fact, confirmed by the inventor, that the after-ejection pressure and age have a linear functional relationship or monotone functional relationship with high probability.

(3) The waveform parameter may be a dicrotic wave height which is pressure difference between a blood pressure at a dicrotic notch and a blood pressure at a dicrotic wave peak.

This enables the blood vessel evaluation information to be obtained by the dicrotic wave height obtained from the pulse waveform based on the fact, confirmed by the inventor, that the after-ejection pressure, which has a linear functional relationship or monotone functional relationship with age with high probability, and the dicrotic wave height have a linear relation.

2.3 Other Features of Each Embodiment of the Present Invention

Each embodiment described above may include any of the following features.

(1) The biological information evaluation apparatus may further comprise:

a blood vessel evaluation information storage section which stores the blood vessel evaluation information; and a change analysis section which analyzes a change in the blood vessel evaluation information based on the blood vessel evaluation information derived by the blood vessel evaluation information deriving section and the blood vessel evaluation information stored in the blood vessel evaluation information storage section.

This enables the change analysis section to analyze changes in the blood vessel evaluation information based on the blood vessel evaluation information stored in the blood vessel evaluation information storage section and the blood vessel evaluation information at the measurement point derived by the blood vessel evaluation information deriving section.

(2) The change analysis section may calculate the amount of change or changing rate of the blood vessel evaluation information relative to the blood vessel evaluation information at a specific point in time.

This enables changes relative to the blood vessel evaluation information at a specific point in time to be analyzed.

(3) The biological information evaluation apparatus may further comprise:

a change amount storage section which stores the amount of change or the changing rate calculated by the change analysis section; and a notification section which notifies the amount of change or the changing rate at several points in time stored in the change amount storage section.

This enables changes relative to the blood vessel evaluation information at a specific point in time to be perceived.

(4) The notification section may notify the amount of change or the changing rate at several points in time stored in the change amount storage section by means of a graph.

This enables changes relative to the blood vessel evaluation information at a specific point in time to be easily perceived.

(5) The biological information evaluation apparatus may further comprise:

an event input section which inputs an occurrence point in time and type of event which is capable of affecting the blood vessel evaluation information; and an event storage section which stores the occurrence point in time and type of event.

(6) The biological information evaluation apparatus may further comprise:

an event input section which inputs an occurrence point in time and type of event which is capable of affecting the blood vessel evaluation information; and an event storage section which stores the occurrence point in time and type of event, and the notification section may notify the type of event in association with the occurrence point in time.

This enables the changes in the blood vessel evaluation information to be perceived in association with the changes with the event which may affect the blood vessel evaluation information.

(7) The biological information evaluation apparatus may further comprise:

an environment sensor section for detecting environmental data which is capable of affecting the blood vessel evaluation information;

an event detection section which detects an occurrence point in time and type of event as an event which is capable of affecting the blood vessel evaluation information, when the environment data reaches a specific range;

a threshold value storage section which stores a threshold value for specifying the specific range corresponding to a type of environmental data detected by the environment sensor section and a type of event; and an event storage section which stores the type and occurrence point in time of the event.

In the present specification, the term "environmental data reaches a specific range" includes not only the case where the numerical value of the environmental data reaches a range specified by two threshold values, but also the case where the numerical value of the environmental data exceeds the threshold value in a positive direction and the case where the numerical value of the environmental data exceeds the threshold value in a negative direction. Any of these cases is selected for each event.

(8) The biological information evaluation apparatus may further comprise:

an environment sensor section for detecting environmental data which is capable of affecting the blood vessel evaluation information;

an event detection section which detects an occurrence point in time and type of event as an event which is capable of affecting the blood vessel evaluation information, when the environment data reaches a specific range;

a threshold value storage section which stores a threshold value for specifying the specific range corresponding to a type of environmental data detected by the environment sensor section and a type of event; and an event storage section which stores the type and occurrence point in time of the event, and the notification section may notify the type of event in association with the occurrence point in time.

This enables the changes in the blood vessel evaluation information to be perceived by associating the changes with an event automatically stored because the event may affect the blood vessel evaluation information.

(9) The biological information evaluation apparatus may further comprise a judgement section which judges whether a change in the blood vessel evaluation information is either a psychogenic change or a change accompanied by an environment or an activity based on a type of event stored in the event storage section, in association with the occurrence point in time, and the blood vessel evaluation information derived by the blood vessel evaluation information deriving section.

This enables the judgement section to judge whether the functional change is either the psychogenic change or change accompanied by environmental conditions which cause hemodynamics to change such as a temperature or activities such as exercise or labor.

(10) The change analysis section may comprise a basal blood vessel evaluation information deriving section which derives the blood vessel evaluation information when the basal metabolism of a subject is in a lowest region during a specific period of time based on the blood vessel evaluation information stored in the blood vessel evaluation information storage section, and a basal blood vessel evaluation information storage section which stores the basal blood vessel evaluation information derived by the basal blood vessel evaluation information deriving section, and the change analysis section may analyze changes in the blood vessel evaluation information based on the blood vessel evaluation information derived by the blood vessel evaluation information deriving section and the basal blood vessel evaluation information stored in the basal blood vessel evaluation information storage section.

This enables the change analysis section to analyze changes in the blood vessel evaluation information based on the basal blood vessel evaluation information stored in the basal blood vessel evaluation information storage section and the blood vessel evaluation information at the measurement point derived by the blood vessel evaluation information deriving section.

(11) The biological information evaluation apparatus may further comprise:

a blood vessel evaluation information storage section which stores the blood vessel evaluation information; and a basal blood vessel evaluation information deriving section which derives the blood vessel evaluation information when the basal metabolism of a subject is in a lowest region during a specific period of time based on the blood vessel evaluation information stored in the blood vessel evaluation information storage section.

This enables the basal blood vessel evaluation information deriving section to derive the blood vessel evaluation information when the basal metabolism of a subject is in the lowest region during a specific period of time, specifically, basal blood vessel evaluation information, using the blood vessel evaluation information stored in the blood vessel evaluation information storage section.

The basal blood vessel evaluation information deriving section may derive blood vessel evaluation information at the time of resting obtained by providing the measurement conditions such as after resting for five minutes during daily activities as the basal blood vessel evaluation information.

(12) The blood vessel evaluation information may be a physiological age of a blood vessel.

This enables the physiological age of the blood vessels to be derived by detecting a specific waveform parameter in the pulse waves.

The physiological age of the blood vessels is an index indicating changes in organic physical property of the blood vessels, for example.

(13) The biological information evaluation apparatus may further comprise:

a data input section into which an actual age of a subject is input; and a comparative analysis section which compares and analyzes the physiological age of the blood vessel based on the physiological age of the blood vessel derived by the blood vessel evaluation information deriving section and the actual age.

This enables the physiological age derived by the blood vessel evaluation information deriving section and the actual age to be compared and analyzed.

(14) The biological information evaluation apparatus may further comprise:

a data input section into which a birth date of a subject is input;

an actual age calculation section which calculates an actual age of the subject based on the birth date of the subject input into the data input section; and a comparative analysis section which compares and analyzes the physiological age of a blood vessel based on the physiological age of the blood vessel derived by the blood vessel evaluation information deriving section and the actual age, and the actual age calculation section may comprise a birth date storage section which stores the birth date of the subject input into the data input section, and a present date calculation section which calculates a present date, and may calculate the actual age of the subject based on the birth date of the subject stored in the birth date storage section and the present date calculated in the present date calculation section.

This enables the actual age automatically calculated by inputting the birth date into the data input section and the physiological age derived by the blood vessel evaluation information deriving section to be compared and analyzed.

(15) The blood vessel evaluation information may be a degree of arteriosclerosis of a blood vessel.

This enables the degree of arteriosclerosis of the blood vessels to be derived by detecting a specific waveform parameter in the pulse waves.

(16) The biological information evaluation apparatus may further comprise:

a data input section into which an actual age of a subject is input; and a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age.

This enables the degree of arteriosclerosis of the blood vessels derived by the blood vessel evaluation information deriving section and the standard degree of arteriosclerosis at the actual age to be compared and analyzed.

(17) The biological information evaluation apparatus may further comprise:

a data input section into which a birth date of a subject is input;

an actual age calculation section which calculates an actual age of the subject based on the birth date of the subject input into the data input section; and a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age, and the actual age calculation section may comprise a birth date storage section which stores the birth date of the subject input into the data input section, and a present date calculation section which calculates a present date, and may calculate the actual age of the subject based on the birth date of the subject stored in the birth date storage section and the present date calculated in the present date calculation section.

This enables the standard degree of arteriosclerosis at the actual age automatically calculated by inputting the birth date into the data input section and the degree of arteriosclerosis of the blood vessels derived by the blood vessel evaluation information deriving section to be compared and analyzed.

(18) The waveform parameter detection section may continuously detect the pulse waveform and may detect the waveform parameter based on the pulse waveform in a period in which a body movement does not affect the pulse waveform.

Therefore, since the detection of the waveform parameter by the waveform parameter detection section is performed using the pulse waveform in a period of time in which there is no effect by body movement, an accurate waveform parameter can be detected without being affected by body movement.

(19) The biological information evaluation apparatus may further comprise a detection instruction input section into which an instruction for the waveform parameter detection section to start detection is input.

This enables the waveform parameter detection section to start detection when the detection instruction is input into the detection instruction input section. Therefore, the waveform parameter can be detected without being affected by body movement or the like by inputting the detection instruction into the detection instruction input section at appropriate timing, whereby an accurate waveform parameter can be detected.

(20) The biological information evaluation apparatus may further comprise a notification section which notifies the pulse waveform or the blood vessel evaluation information.

This enables the blood vessel evaluation information derived by the blood vessel evaluation information deriving section or pulse waveform to be perceived.

(21) The biological information evaluation apparatus may further comprise a notification section which notifies an analysis result in the change analysis section.

This enables the analysis results by the change analysis section to be perceived.

(22) The biological information evaluation apparatus may further comprise a notification section which notifies an analysis result in the comparative analysis section.

This enables the analysis results by the comparative analysis section to be perceived.

Figure 5:
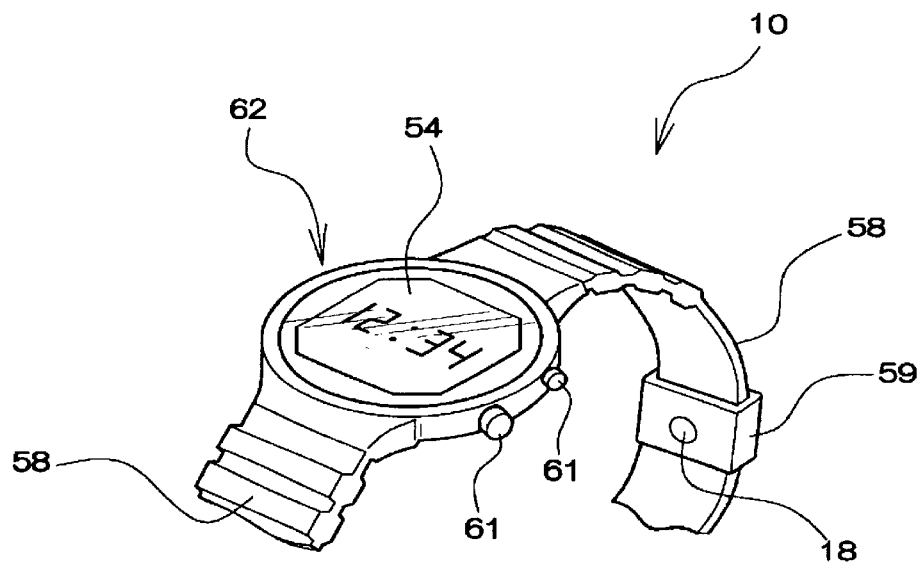
FIG. 5 is an oblique view showing the appearance of a biological information evaluation apparatus according to an embodiment A.
Figure 6:
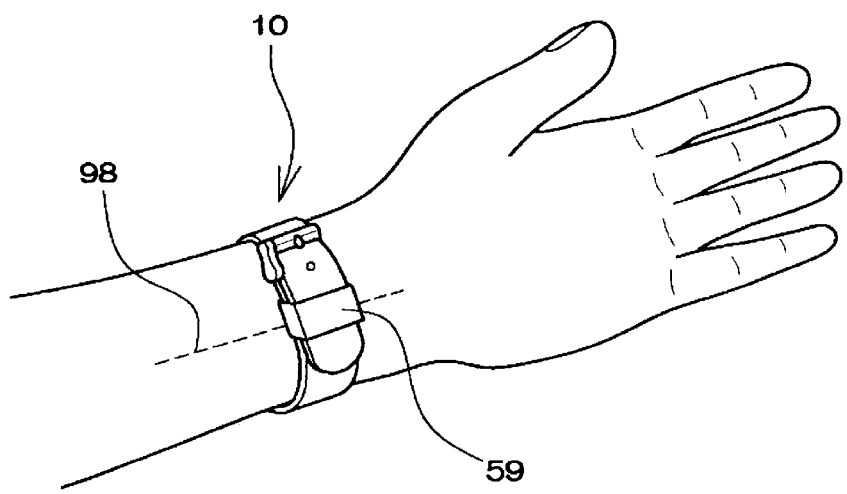
FIG. 6 is an oblique view showing the biological information evaluation apparatus shown in FIG. 5 worn on the wrist.

3. Embodiment A 3.1 External Structure of Biological Information Evaluation Apparatus A biological information evaluation apparatus according to the present embodiment may be formed in the shape of a wristwatch as shown in FIGS. 5 and 6, for example. FIG. 5 is an oblique view showing the appearance of a biological information evaluation apparatus 10. FIG. 6 is an oblique view showing the biological information evaluation apparatus 10 worn on the wrist.

As shown in these figures, the biological information evaluation apparatus 10 includes a body section 62, a pair of bands 58 attached to the body section 62, and a sensor holding section 59 suspended around the band 58 so as to be able to move along the bands 58. A pulse wave sensor 18 such as a pressure sensor is provided to the sensor holding section 59 so as to project from the sensor holding section 59. The pulse wave sensor 18 is connected to the body section 62 through wiring (not shown) such as an FPC (flexible printed circuit) board which transmits signals detected by the pulse wave sensor 18. The body section 62 is equipped with a clock IC (not shown) A display section 54 as a notification section can display time information output from the clock IC, as shown in FIG. 5. Operation buttons 61 for performing various types of operations are used for changing over between a measurement mode for measuring the pulse waves and a clock mode for displaying time or to input various types of information, for example.

When using the biological information evaluation apparatus 10, the biological information evaluation apparatus 10 with a wristwatch structure is wound around the wrist of a subject so that the sensor holding section 59 is located close to the radial artery 98, as shown in FIG. 6. The sensor holding section 59 is positioned by moving the sensor holding section 59 along the bands 58 so that the pulse wave sensor 18 provided on the sensor holding section 59 is located above the radial artery 98, for example.

When the pulse wave sensor 18 is pressed against the radial artery 98 of the subject, pulse waves corresponding to the vibration of the blood vessel wall accompanied by the changes in the blood flow in the artery are transmitted to the pulse wave sensor 18, thereby enebling the biological information evaluation apparatus 10 to detect the pulse wave at any time. Note that the pulse waveform can be detected as a waveform having almost the same shape as the blood pressure waveform in the blood vessels.

3.2 Functional Structure of Biological Information Evaluation Apparatus

Figure 7:
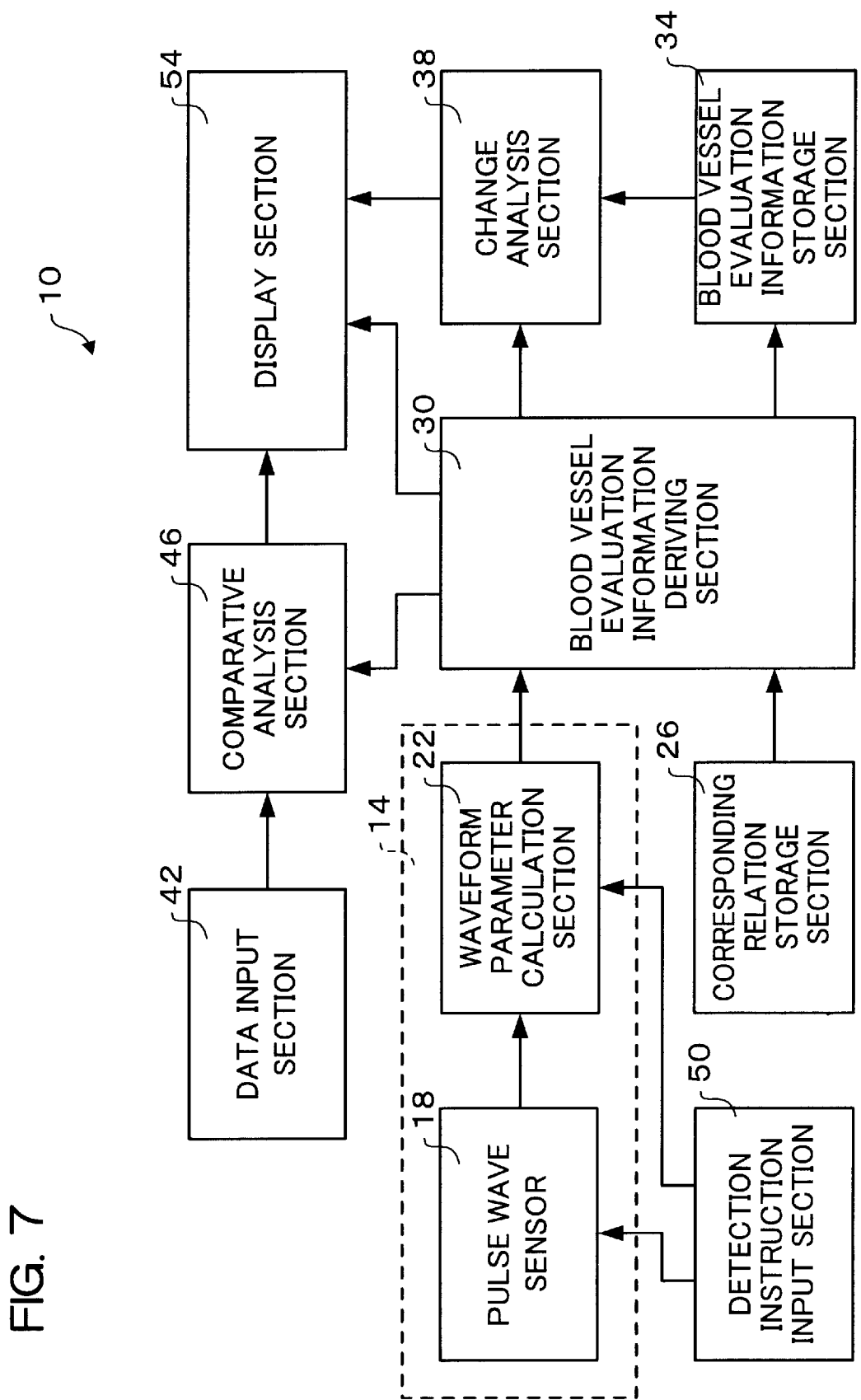
FIG. 7 is a block diagram showing the functional structure of the biological information evaluation apparatus according to the embodiment A.

FIG. 7 is a block diagram showing the functional structure of the biological information evaluation apparatus 10 according to the present embodiment. As shown in FIG. 7, in addition to each section as described above, the biological information evaluation apparatus 10 includes a waveform parameter detection section 14 including the pulse wave sensor 18 such as a pressure sensor and a waveform parameter calculation section 22, a corresponding relation storage section 26, a blood vessel evaluation information deriving section 30, a data input section 42, a comparative analysis section 46, a detection instruction input section 50, a blood vessel evaluation information storage section 34, and a change analysis section 38. Each of these sections maybe incorporated in the body section 62, or individually formed and electrically connected to the pulse wave sensor 18, display section 54 as the notification section, or the like.

The waveform parameter detection section 14 includes the pulse wave sensor 18 and the waveform parameter calculation section 22. The waveform parameter calculation section 22 calculates at least either the after-ejection pressure ratio or the dicrotic wave height ratio as the waveform parameter from the pulse waveform detected by the pulse wave sensor 18. As described using FIG. 1, the after-ejection pressure ratio $\Delta BP_P$ is the pressure difference between the systolic blood pressure $BP_{sys}$ and the blood pressure at the dicrotic notch normalized by the pulse pressure $\Delta BP$. The dicrotic wave height $\Delta BP_D$ is the pressure difference between the blood pressure at the dicrotic notch and the blood pressure at the dicrotic wave peak normalized by the pulse pressure $\Delta BP$. The following description of the present embodiment illustrates an example using the after-ejection pressure ratio as the waveform parameter. The waveform parameter calculation section 22 includes a CPU and a memory in which a program for operating the CPU is stored, for example.

The detection instruction input section 50 is formed so that the instruction for allowing the waveform parameter detection section 14 to start detection is input by the operation of the operation buttons 61 or using a voice command utilizing a microphone (not shown), for example. When the detection instruction is input into the detection instruction input section 50, the after-ejection pressure ratio is detected as the waveform parameter by the operation of the pulse wave sensor 18 and the waveform parameter calculation section 22.

The corresponding relation storage section 26 stores in advance the corresponding relation between the after-ejection pressure ratio as the waveform parameter and the blood vessel evaluation information. For example, the corresponding relation storage section stores the relation between the physiological age or degree of arteriosclerosis as the blood vessel evaluation information and the after-ejection pressure ratio as a linear equation or a monotone function which either increases or decreases monotonously. The corresponding relation storage section may store the physiological age or degree of arteriosclerosis corresponding to various after-ejection pressure ratios. The corresponding relation storage section 26 can be formed using at least any of a semiconductor memory and a storage medium utilizing magnetism or light.

The blood vessel evaluation information deriving section 30 derives the physiological age or degree of arteriosclerosis as the blood vessel evaluation information based on the after-ejection pressure ratio detected by the waveform parameter detection section 14 and the corresponding relation stored in the corresponding relation storage section 26, specifically, the corresponding relation between the physiological age or degree of arteriosclerosis as the blood vessel evaluation information and the after-ejection pressure ratio. The blood vessel evaluation information deriving section 30 includes a CPU (Central Processing Unit) and a memory in which a program for operating the CPU is stored, for example.

The data input section 42 is formed so that the subject's actual age is input by the operation of the operation buttons 61 or using a voice command entered through a microphone (not shown), for example. The data input section 42 outputs the actual age to the comparative analysis section 46 as data.

In the case where the physiological age is output from the blood vessel evaluation information deriving section 30 as the blood vessel evaluation information, the comparative analysis section 46 compares the subject's actual age input into the data input section 42 with the physiological age of the blood vessels derived by the blood vessel evaluation information deriving section 30 and analyzes this data. The comparative analysis section 46 outputs the difference therebetween to the display section 54 as the notification section, for example. The comparative analysis section 46 stores standard degrees of arteriosclerosis which are standard values for the degree of arteriosclerosis corresponding to each age. In the case where the degree of arteriosclerosis is output from the blood vessel evaluation information deriving section 30 as the blood vessel evaluation information, the comparative analysis section 46 reads out the standard degree of arteriosclerosis corresponding to the actual age of the subject input into the data input section 42 from the data stored therein. The comparative analysis section 46 compares the standard degree of arteriosclerosis with the degree of arteriosclerosis derived by the blood vessel evaluation information deriving section 30, analyzes this information, and outputs the difference therebetween to the display section 54, for example. The comparative analysis section 46 includes a CPU and a memory in which a program for operating the CPU is stored.

The blood vessel evaluation information storage section 34 includes a semiconductor memory or a storage medium utilizing magnetism or light and a semiconductor memory in combination. The blood vessel evaluation information storage section 34 stores the physiological age or degree of arteriosclerosis output from the blood vessel evaluation information deriving section 30 as the previously measured blood vessel evaluation information.

The change analysis section 38 analyzes changes in the blood vessel evaluation information based on the physiological age or degree of arteriosclerosis derived by the blood vessel evaluation information deriving section 30 as the blood vessel evaluation information and the physiological age or degree of arteriosclerosis stored in the blood vessel evaluation information storage section 34 as the blood vessel evaluation information, and calculates the amount of change, changing rate, and the like. For example, the change analysis section 38 calculates the amount of change, changing rate, and the like of the physiological age at present derived by the blood vessel evaluation information deriving section 30 to the physiological age at the time of starting the measurement stored in the blood vessel evaluation information storage section 34. The results are input to the display section 54.

The display section 54 as the notification section displays the physiological age or degree of arteriosclerosis derived by the blood vessel evaluation information deriving section 30 as the blood vessel evaluation information, the analysis results by the comparative analysis section, or the analysis results by the change analysis section 38 using characters, symbols, graphs, or the like.

3.3 Operation of Biological Information Evaluation Apparatus

The biological information evaluation apparatus 10 evaluates the blood vessels of the subject by operating as described below, for example.

The bands of the biological information evaluation apparatus 10 formed in the shape of a watch are wound around the wrist so that the sensor holding section 59 is located close to the radial artery 98.

The actual age of the subject is input into the data input section 42, formed so as to allow the operation buttons to be operated or a voice command to be input through a microphone, by operating the operation buttons or inputting a voice command. The data is stored in the comparative analysis section 46.

After resting for an appropriate period of time, a detection instruction is input to the detection instruction input section 50 when there is no body movement by specific operation of the operation buttons 61 or vocalization of a specific voice pattern.

When the detection instruction is input, the pulse wave sensor 18 such as a pressure sensor detects the vibration waveform of the blood vessel wall accompanied by the blood flow, specifically, the pulse waveform in the artery in the wrist such as the radial artery 98 as the pressure waveform. The waveform parameter calculation section 22 calculates the waveform parameter such as the after-ejection pressure ratio based on the pressure waveform. The after-ejection pressure ratio as the waveform parameter is thus detected by the waveform parameter detection section 14 including the pulse wave sensor 18 and the waveform parameter calculation section 22. Therefore, detection of the waveform parameter without being affected by body movement or the like can be started by inputting the detection instruction into the detection instruction input section 50 at an appropriate time when there are no effects from body movement or the like, whereby an accurate waveform parameter can be detected.

The blood vessel evaluation information deriving section 30 derives the physiological age or degree of arteriosclerosis as the blood vessel evaluation information based on the after-ejection pressure ratio detected by the waveform parameter detection section 14 and the corresponding relation between the after-ejection pressure ratio and the physiological age (or degree of arteriosclerosis) stored in the corresponding relation storage section 26.

The display section 54 as the notification section including a liquid crystal display device, for example, displays the physiological age or degree of arteriosclerosis as the blood vessel evaluation information derived by the blood vessel evaluation information deriving section 30 using characters, graphs, or the like.

The physiological age or degree of arteriosclerosis as the blood vessel evaluation information derived by the blood vessel evaluation information deriving section 30 is input to the comparative analysis section. The comparative analysis section compares this physiological age or degree of arteriosclerosis with the actual age of the subject or standard degree of arteriosclerosis at the actual age of the subject which is input in advance and analyzes this information. The results are input to the display section 54 as the notification section and displayed together with the physiological age or degree of arteriosclerosis as the blood vessel evaluation information.

The physiological age or degree of arteriosclerosis as the blood vessel evaluation information derived by the blood vessel evaluation information deriving section 30 is also input to the blood vessel evaluation information storage section 34 and the change analysis section 38. The physiological age or degree of arteriosclerosis input to the blood vessel evaluation information storage section 34 is stored for at least a specified period of time. The change analysis section 38 compares and analyzes the physiological age or degree of arteriosclerosis input thereto with the physiological age or degree of arteriosclerosis as the blood vessel evaluation information stored in the blood vessel evaluation information storage section 34, and derives the amount of change or changing rate of the physiological age or degree of arteriosclerosis, for example. The results are input to the display section 54 and displayed therein together with the physiological age or degree of arteriosclerosis as the blood vessel evaluation information.

3.4 Modification Example of Embodiment A 3.4.1

Figure 8:
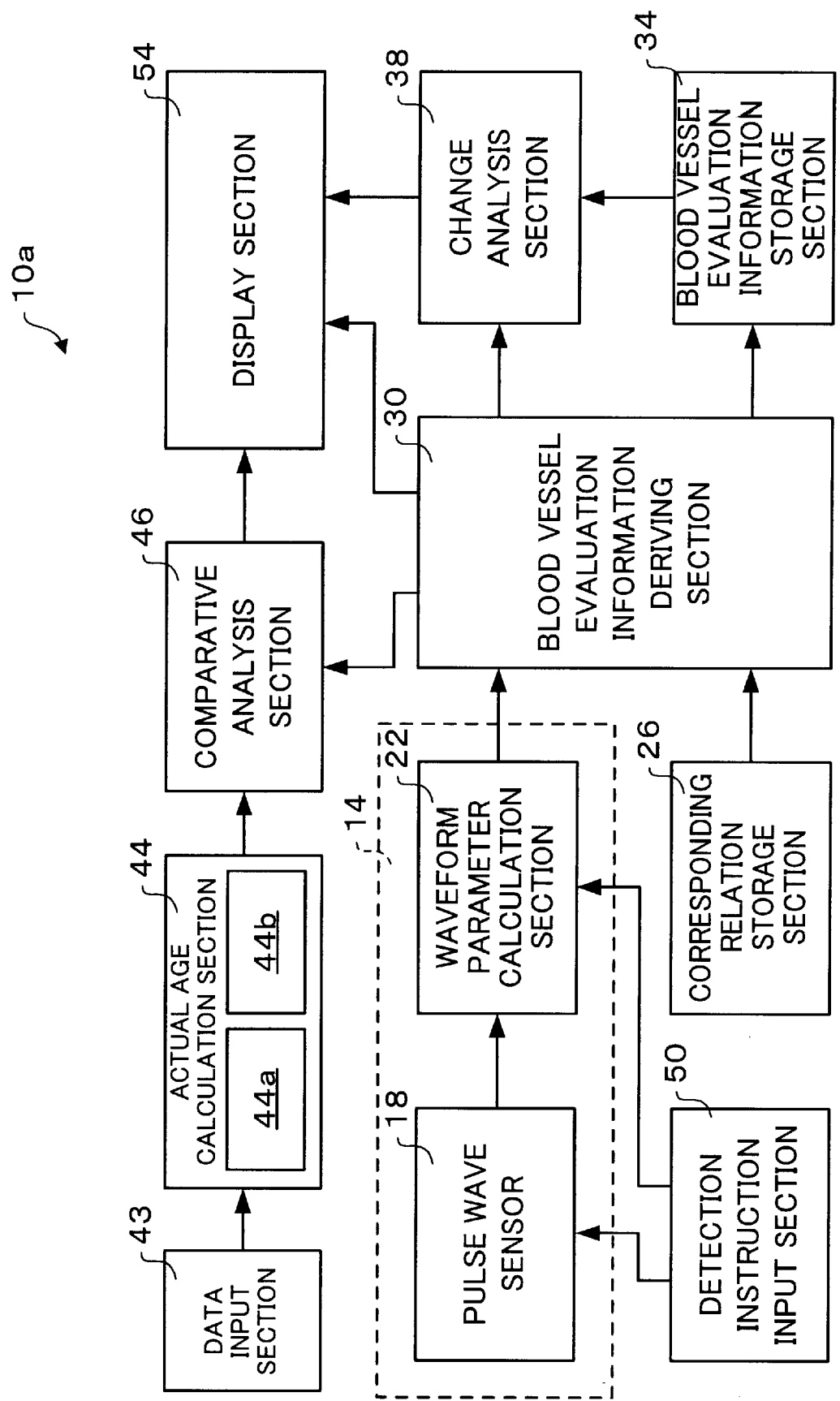
FIG. 8 is a block diagram showing the functional structure of a biological information evaluation apparatus according to a modification example of the embodiment A.

The above description of the present embodiment illustrates an example in which the actual age of the subject is input to the data input section 42. The following modification example is possible, relating to this point. FIG. 8 is a block diagram showing the functional structure of a biological information evaluation apparatus 10a in this modification example. In the biological information evaluation apparatus 10a, a data input section 43 is formed so that the birth date of the subject is input into the data input section 43, and an actual age calculation section 44 is additionally provided.

The actual age calculation section 44 calculates the actual age of the subject from the birth date of the subject input to the data input section. More specifically, the actual age calculation section 44 includes a birth date storage section 44a and a present date calculation section 44b, and calculates the actual age of the subject based on the birth date of the subject stored in the birth date storage section 44a and the present date calculated in the present date calculation section 44b.

The comparative analysis section 46 compares the physiological age or degree of arteriosclerosis of the blood vessels based on the physiological age or degree of arteriosclerosis of the blood vessels derived by the blood vessel evaluation information deriving section 30 and the actual age of the subject calculated by the actual age calculation section 44 and analyzes this information. Except for the above point, the biological information evaluation apparatus in this modification example has the same structure as that in the embodiment A and operates in the same manner.

3.4.2

Figure 9:
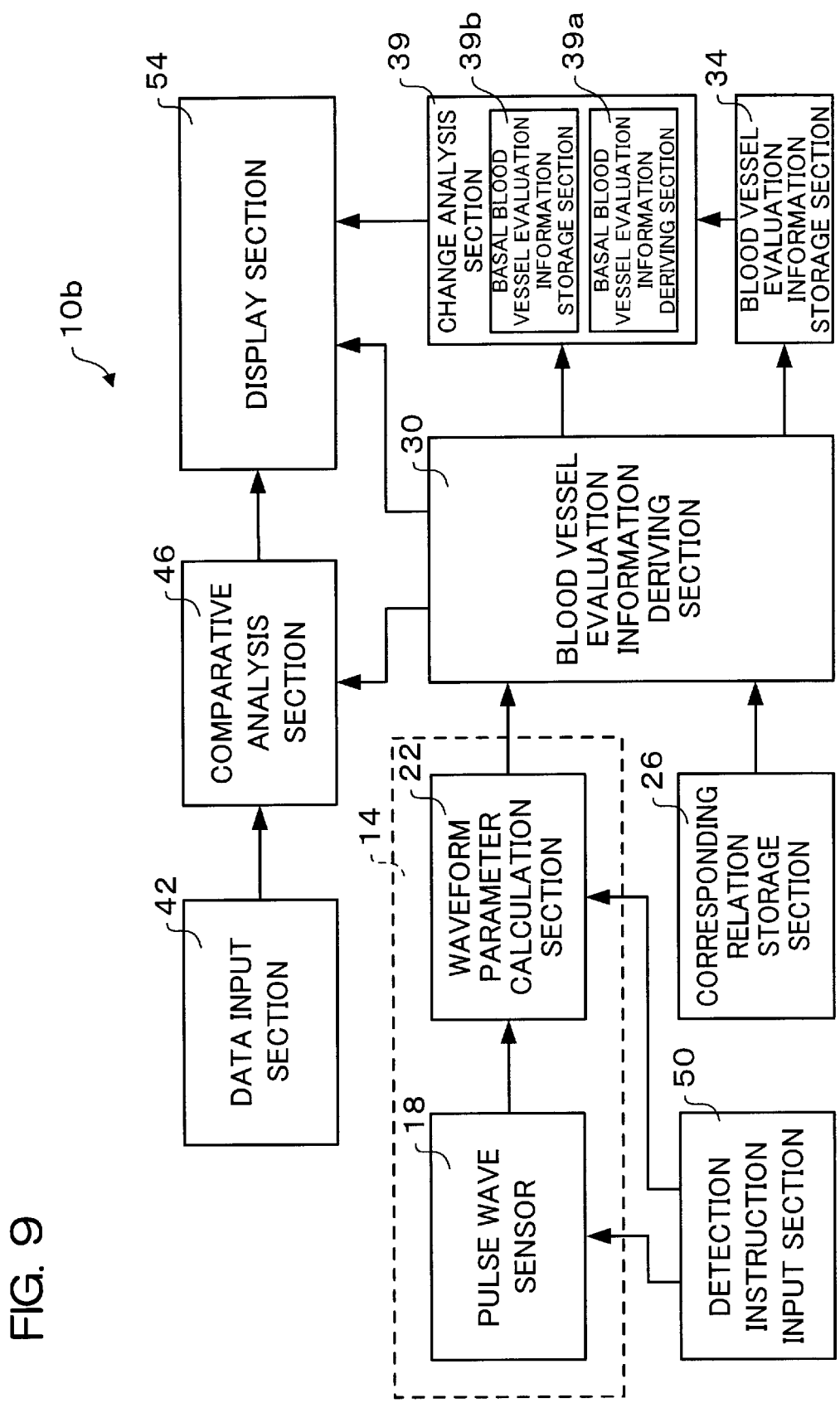
FIG. 9 is a block diagram showing the functional structure of a biological information evaluation apparatus according to another modification example of the embodiment A.

A modification example provided with a change analysis section 39 as described below is also possible. FIG. 9 is a block diagram showing the functional structure of a biological information evaluation apparatus 10b in this modification example. In the biological information evaluation apparatus 10b, the change analysis section 39 includes a basal blood vessel evaluation information deriving section 39a and a basal blood vessel evaluation information storage section 39b.

The basal blood vessel evaluation information deriving section 39a derives the blood vessel evaluation information such as the physiological age or degree of arteriosclerosis of the blood vessels when the basal metabolism of the subject is in the lowest region in a specified period of time such as in one day based on the blood vessel evaluation information stored in the blood vessel evaluation information storage section 34. Note that the basal metabolism in humans generally reaches the lowest state, specifically, the basal state, while sleeping from 2 AM to 4 AM in any day. The basal blood vessel evaluation information is the blood vessel evaluation information such as the physiological age or degree of arteriosclerosis of the blood vessels in the basal state in any day, for example.

The basal blood vessel evaluation information deriving section 39a is not limited to one which derives the basal blood vessel evaluation information when the basal metabolism of the subject is in the lowest region in any day. The basal blood vessel evaluation information deriving section 39a may derive blood vessel evaluation information when the basal metabolism of the subject is in the lowest region during a specified period of time such as one week, one month, three months, or one year as the basal blood vessel evaluation information.

The basal blood vessel evaluation information deriving section 39*a* may derive blood vessel evaluation information at the time of resting obtained by providing the measurement conditions such as after resting for five minutes during daily activities as the basal blood vessel evaluation information.

The basal blood vessel evaluation information storage section 39*b* stores the basal blood vessel evaluation information derived by the basal blood vessel evaluation information deriving section 39*a*.

The change analysis section 39 analyzes changes in the blood vessel evaluation information such as the physiological age or degree of arteriosclerosis of the blood vessels based on the blood vessel evaluation information derived by the blood vessel evaluation information deriving section 30 and the basal blood vessel evaluation information stored in the basal blood vessel evaluation information storage section 39*b*, and outputs the results to the display section 54.

The change analysis section 39 may store the blood vessel evaluation information derived as the basal blood vessel evaluation information when the basal metabolism is in the lowest region during a period of time such as one day, one week, one month, three months, or one year in the basal blood vessel evaluation information storage section 39*b*. The change analysis section 39 may compare the basal blood vessel evaluation information with the basal blood vessel evaluation information derived after a specified period of time such as one month, six months, or one year, and output the results to the display section 54.

Except for the above point, the biological information evaluation apparatus in this modification example has the same structure as that in the embodiment A and operates in the same manner.

3.4.3

The above description in the present embodiment illustrates an example in which the waveform parameter detected by the waveform parameter detection section 14 and used for the blood vessel evaluation information deriving section 30 to derive the blood vessel evaluation information is the after-ejection pressure ratio $\Delta BP_P/\Delta BP$. However, the waveform parameter detected by the waveform parameter detection section 14 and used for the blood vessel evaluation information deriving section 30 to derive the blood vessel evaluation information may be the dicrotic wave height ratio $\Delta BP_D/\Delta BP$. As described in "1. <Basic principle>", in the case of using the dicrotic wave height ratio as the waveform parameter, the physiological age or degree of arteriosclerosis as the blood vessel evaluation information can also be derived.

3.4.4

The above description of the present embodiment illustrates an example using a pressure sensor as the pulse wave sensor. Since the pulse waveform is almost similar to the waveform of changes in the amount of blood flow, a photosensor formed so as to irradiate the artery and detect changes in the amount of reflected light or amount of transmitted light due to blood in the artery may be used as the pulse wave sensor in place of the pressure sensor.

Such a photosensor may be formed using an LED (light-emitting diode) and a phototransistor, for example. The light receiving level is changed corresponding to the amount of blood flow by selecting the emission wavelength of the LED near the reflection or absorption wavelength peak of hemoglobin in the blood and selecting the light receiving wavelength region of the phototransistor near the reflection or absorption wavelength peak of hemoglobin. The pulse waveform can be detected by thus detecting the light receiving level.

The biological information evaluation apparatus 10 of the present embodiment uses the after-ejection pressure ratio $\Delta BP_P/\Delta BP$, which is the after-ejection pressure normalized by the pulse pressure, or the dicrotic wave height ratio $\Delta BP_D/\Delta BP$, which is the dicrotic wave height normalized by the pulse pressure, as the waveform parameter for obtaining the blood vessel evaluation information. Therefore, there is no need to use a sensor which detects the absolute blood pressure as the pulse wave sensor. Because of this, a biological information evaluation apparatus which can exhibit the same effect as the above-described biological information evaluation apparatus can be formed by using a photoelectric sensor capable of obtaining a waveform with the same shape as the blood pressure waveform as the pulse wave sensor.

Assuming that the peak amplitudes of the waveform obtained by calculating the second derivative of the pulse waveform obtained using the above photosensor (photoelectric plethysmogram waveform) within one period are a, b, c, d, and e in the order of size, each of b/a and d/a can be used as the blood vessel evaluation index. Specifically, b/a indicates the organic changes of the blood vessel, and d/a indicates the functional changes of blood vessel properties.

3.4.5

The above description of the present embodiment illustrates an example in which the waveform parameter detection section 14 detects the waveform parameter when there is little effect from body movement by the instruction input to the detection instruction input section 50 when there is little body movement. However, the waveform parameter detection section 14 maybe formed so as to continuously measure the pulse waveform and detect the waveform parameter based on the pulse waveform in a period in which body movement does not affect the pulse waveform. This enables the waveform parameter detection section 14 to detect an accurate waveform parameter without being affected by body movement. In this case, the above detection instruction input section 50 may be omitted.

3.4.6

The above description of the present embodiment illustrates the case where the radial artery 98 is the artery in which the pulse wave sensor detects vibration. However, the artery in which the pulse wave sensor detects the pulse wave may be any artery in the extremities and fingers such as the ulnar artery in the wrist, the palmar digital artery which is an artery in the finger, the brachial artery in the upper arm, or the popliteal artery in the lower limbs. The artery in which the pulse wave sensor detects the pulse wave may be another artery which runs near the body surface such as the carotid artery or the femoral artery.

3.4.7

The above description of the present embodiment illustrates an example in which the display section 54 including a liquid crystal display device, for example, is used as the notification section, and the display section 54 notifies the results by displaying characters, graph, or the like. However, a notification section including the display section 54 and a printer or a voice synthesizer and a speaker may be used instead of using the display section 54, and the notification section may display or print out such information using characters or graphs, or notify using voice output.

3.5 Effect of Embodiment A

As described above, the biological information evaluation apparatus 10 according to the present embodiment stores in advance the corresponding relation between a specific waveform parameter in the pulse waveform and the blood vessel evaluation information in the corresponding relation storage section 26. The blood vessel evaluation information deriving section 30 uniquely derives the blood vessel evaluation information by applying the detected waveform parameter to the corresponding relation. Therefore, the blood vessel evaluation information can be derived without the need for a large memory capacity or a large number of arithmetic operations.

Moreover, the biological information evaluation apparatus 10 uses the after-ejection pressure ratio $\Delta BP_P/\Delta BP$, which is the after-ejection pressure normalized by the pulse pressure, or the dicrotic wave height ratio $\Delta BP_D/\Delta BP$, which is the dicrotic wave height normalized by the pulse pressure, as the waveform parameter for obtaining the blood vessel evaluation information. Therefore, the wave form parameter can be obtained from the pulse waveform, whereby a structure for detecting the absolute blood pressure is not needed.

4. Embodiment B

The embodiment B differs from the embodiment A as to the external structure and the functional structure to some extent. In the following description, features differing from the embodiment A are mainly described. Other features are the same as in the embodiment A, and description of these features is omitted. In the drawings, corresponding sections are indicated using the same symbols.

4.1 External Structure of Biological Information Evaluation Apparatus

Figure 10:
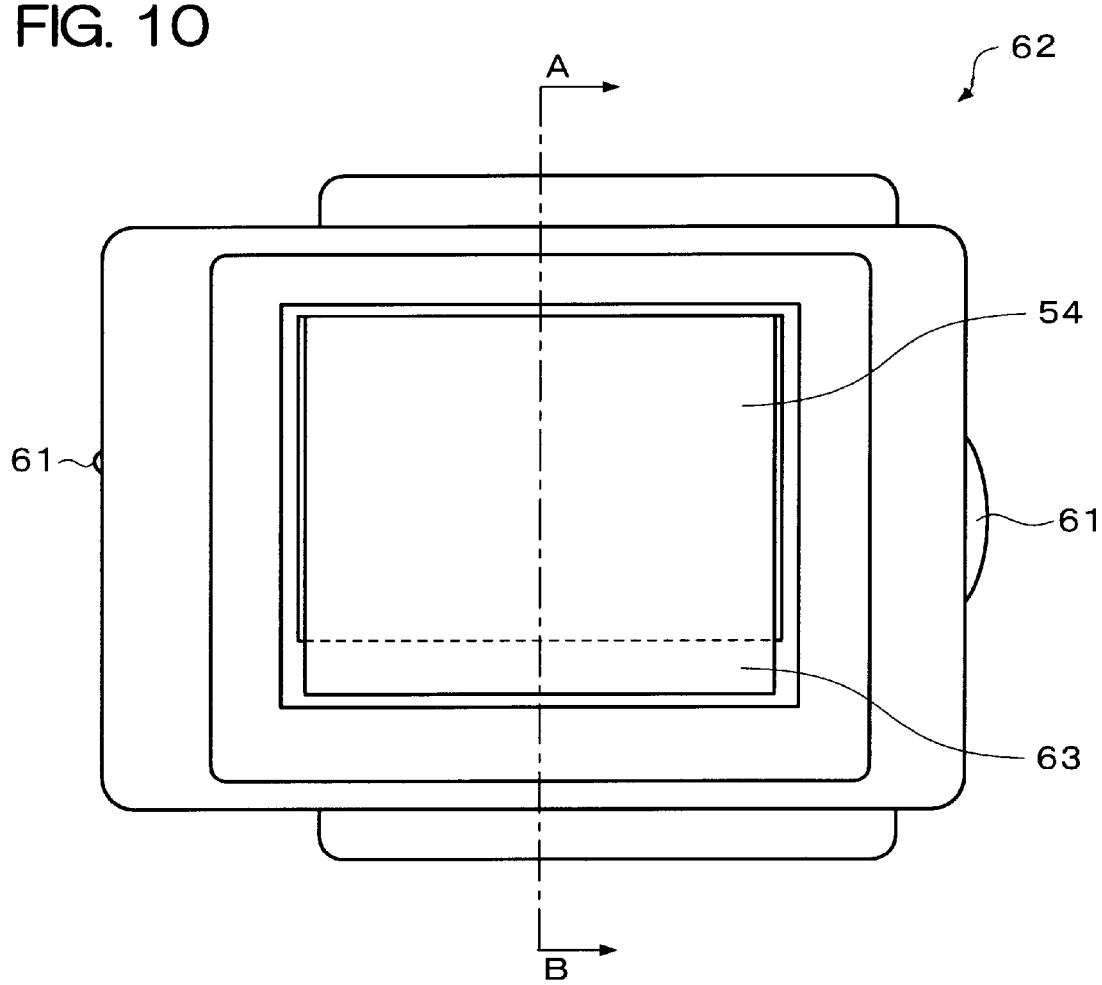
FIG. 10 is a plan view showing a body section of a biological information evaluation apparatus according to an embodiment B.
Figure 11:
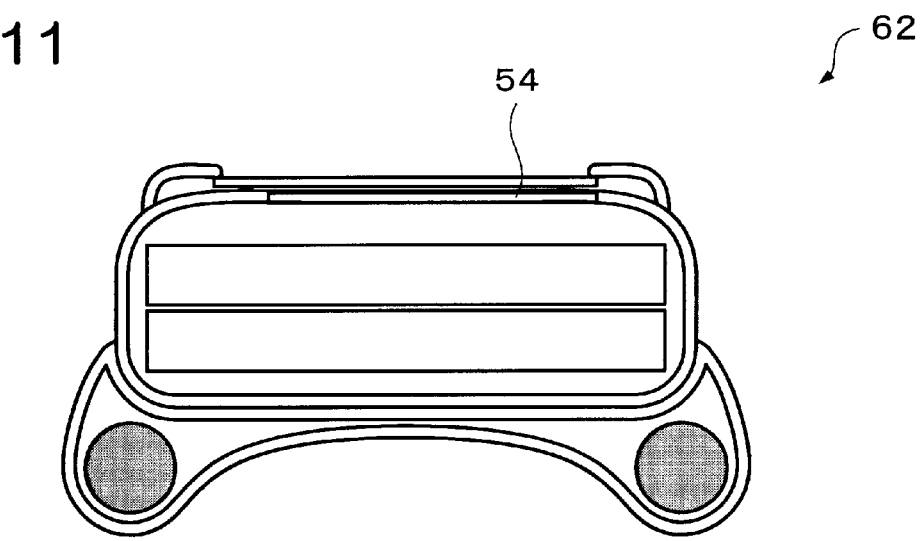
FIG. 11 is a schematic cross-sectional view corresponding to the position along the line A–B shown in FIG. 10.

A biological information evaluation apparatus according to the present embodiment is also formed in the shape of a wristwatch in the same manner as in the embodiment A. FIG. 10 is a plan view showing a body section 62 of a biological information evaluation apparatus 40. FIG. 11 is a schematic cross-sectional view corresponding to the position along the line A–B shown in FIG. 10. FIGS. 12 to 15 are views showing display examples of the display section 54 as the notification section.

Although not shown in the figures, bands are attached to the body section 62 in the present embodiment. A sensor holding section is provided capable of moving along the bands. A pulse wave sensor such as a pressure sensor is provided on the sensor holding section. The operation buttons 61 for performing various types of operations are provided on the sides of the body section 62, and a touch panel 63 is provided in the region almost overlapping the display section 54, thereby enabling various types of input operations.

4.2 Functional Structure of Biological Information Evaluation Apparatus

Figure 16:
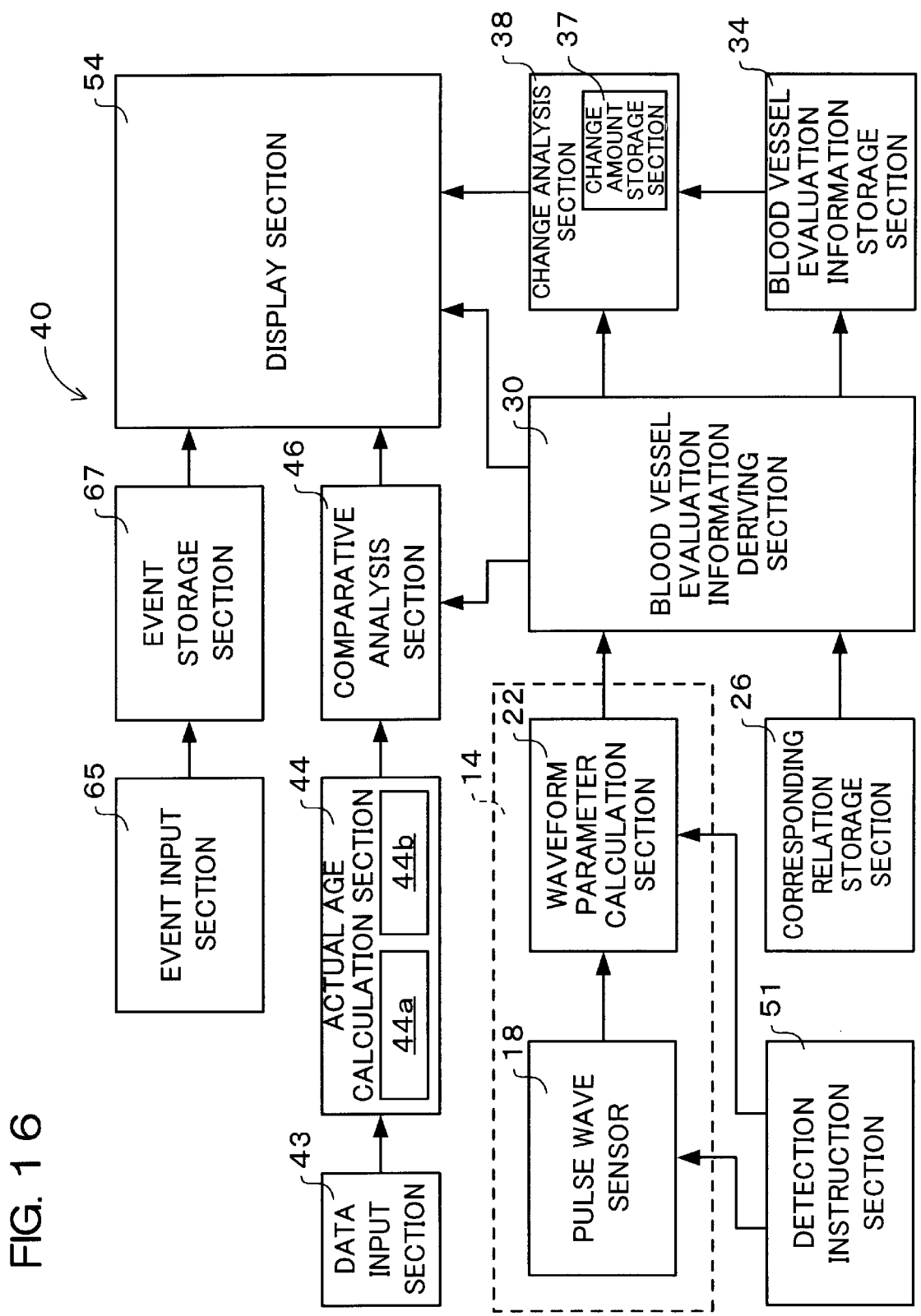
FIG. 16 is a block diagram showing the functional structure of the biological information evaluation apparatus according to the embodiment B.

FIG. 16 is a block diagram showing the functional structure of the biological information evaluation apparatus 40 according to the present embodiment. As shown in FIG. 16, the biological information evaluation apparatus 40 includes an event input section 65, an event storage section 67, and a change amount storage section 37 in addition to each block provided in the biological information evaluation apparatus 10 of the embodiment A. A detection instruction section 51 is provided in place of the detection instruction input section 50.

The event input section 65 includes specific regions of the touch panel 63 corresponding to the operation modes of the biological information evaluation apparatus 40. The occurrence points in time and the types of events which may affect the blood vessel evaluation information such as mealtime, exercise, administration of medicine, urination, and sleep can be input to the event input section 65. In an operation mode corresponding to the display example shown in FIG. 12, for example, pressing a button on which an icon of a vial with a cross is displayed allows administration of medicine at this time to be input. Pressing a button on which a knife and a fork are displayed allows mealtime at this time to be input.

The event storage section 67 stores the types of events input to the event input section 65 while associating these events with the occurrence points. The event storage section 67 may be formed using a semiconductor memory or a storage medium utilizing magnetism or light. Information stored in the event storage section 67 is input to the display section 54.

The change amount storage section 37 stores the amount of change or changing rate calculated in the change analysis section 38. The content of the change amount storage section 37 is input to the display section 54. The change amount storage section 37 may be formed using a semiconductor memory or a storage medium utilizing magnetism or light.

Figure 12:
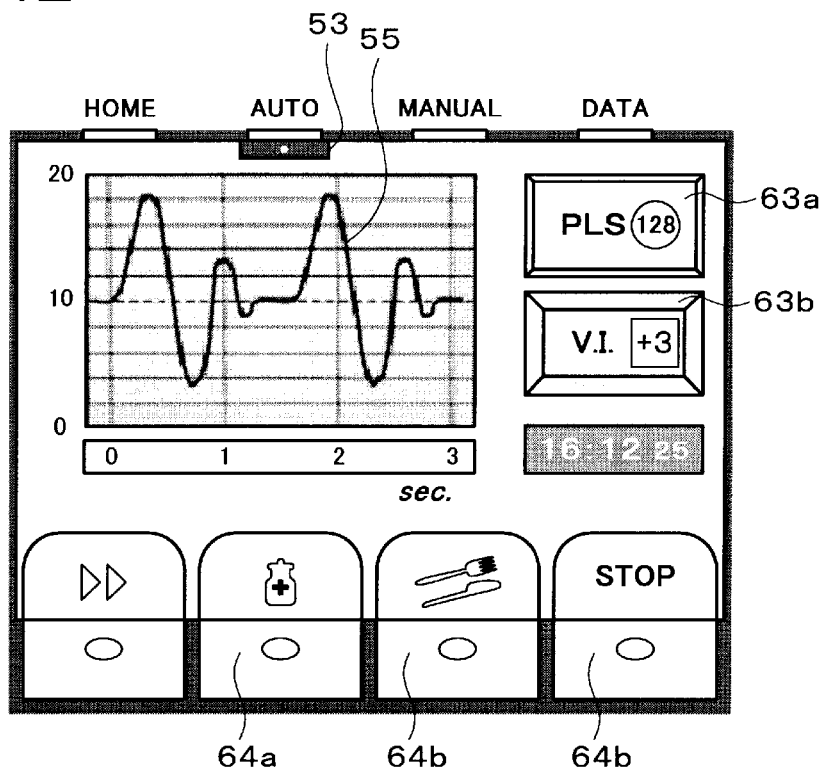
FIG. 12 is a view showing a modification example of a display section.
Figure 13:
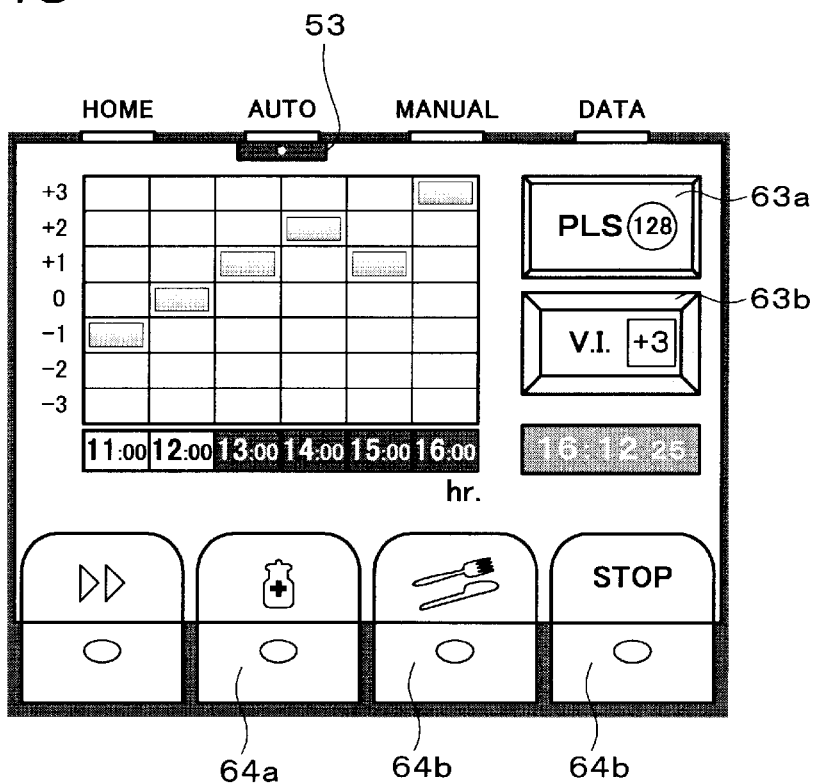
FIG. 13 is a view showing a modification example of the display section.

The display section 54 includes a liquid crystal display device, a display control circuit, and the like. The display section 54 may have a function of displaying a pulse waveform 55 in addition to the functions illustrated in the embodiment A, as shown in FIG. 12. The display section 54 may display the amount of change or changing rate of the blood vessel evaluation information at several points in time stored in the change amount storage section 37 using a graph, as shown in FIG. 13. In this display, the physiological age is used as the blood vessel evaluation information, and the differences between the physiological age measured every hour and the actual age are displayed for the past several hours. "PLS 128" shown in this display indicates that the present pulse rate per minute is 128 beats. "V.I.+3" indicates that the present value of the physiological age as the blood vessel evaluation information (Vascular Index) is three years more than the value of the actual age used as the standard.

Figure 14:
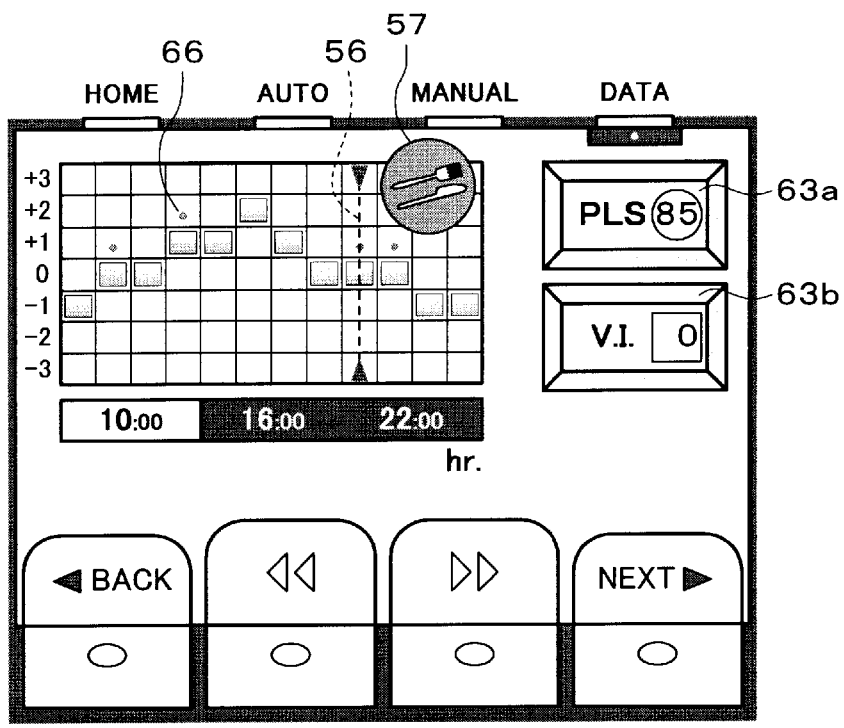
FIG. 14 is a view showing a modification example of the display section.

The display section 54 may indicate the presence of the event input by the event input section using a specific symbol such as a small circle in a mode in which the amount of change or changing rate of the blood vessel evaluation information for the past several points is displayed, as shown in FIG. 14. When a cursor line 56 is positioned on the small circle, the type of event is displayed in a pop up window 57. FIG. 14 shows that mealtime was between 16:00 and 22:00. In a state in which the cursor line is displayed, the pulse rate and the absolute value of the blood vessel evaluation information at a point corresponding to the cursor line are displayed. In FIG. 14, "PLS 85" and "V.I. 0" indicate that the pulse rate is 85 beats and the physiological age as the blood vessel evaluation information is equal to the actual age used as the comparative standard at a point corresponding to the cursor line.

The detection instruction section 51 allows the pulse wave sensor 18 and the waveform parameter calculation section 22 to operate at a predetermined timing, thereby allowing the after-ejection pressure ratio to be detected as the waveform parameter.

4.3 Operation of Biological Information Evaluation Apparatus

The measurement operations of the biological information evaluation apparatus 40 at each point are almost the same as those of the biological information evaluation apparatus of the embodiment A. The operations of the biological information evaluation apparatus 40 differ from the operations in the embodiment A in that the biological information evaluation apparatus 40 has a plurality of operation modes including the data display mode.

The biological information evaluation apparatus of the present embodiment operates in four operation modes including a home mode, auto-measurement mode, manual measurement mode, and data display mode. Each operation mode is selected by pressing the touch panel near the characters indicating these modes displayed on the display section as buttons. The characters "HOME", "AUTO", "MANUAL", and "DATA" displayed near the upper side of the display section are used to indicate which of these modes is selected with a highlight displayed under the characters of the selected mode. For example, FIGS. 12 and 13 show that the "AUTO" mode is selected. Each mode is simply described below.

Figure 15:
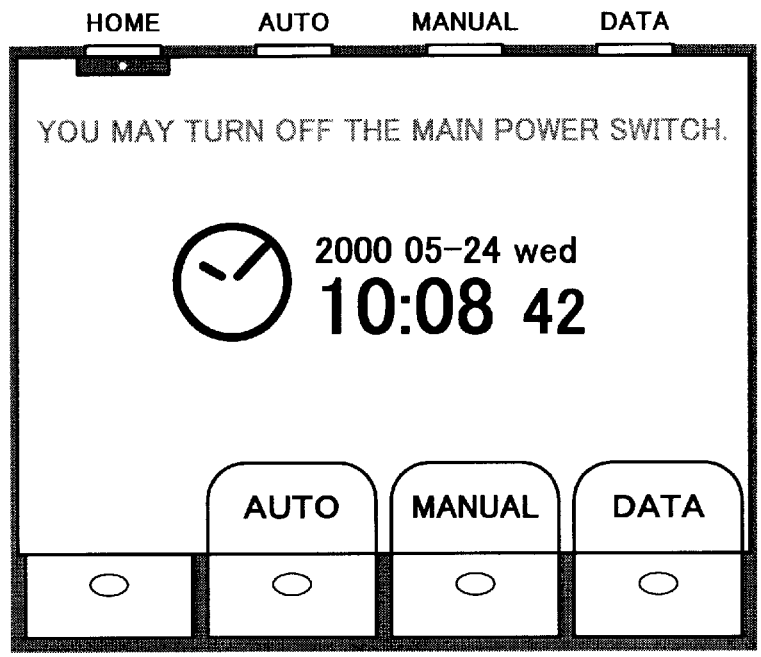
FIG. 15 is a view showing a modification example of the display section.

The home mode is used to select any of three other modes in which a display shown in FIG. 15 is displayed on the display section 54, for example. The home mode is automatically selected at the time of starting the operation. The home mode is also selected by pressing the "HOME" button on the touch panel in other operation modes.

The auto-measurement mode is selected by pressing the "AUTO" button on the touch panel in the home mode. In the auto-measurement mode, measurement is automatically performed every 10 minutes for 24 hours, for example. FIGS. 12 and 13 show display examples of the display section 54 in the auto-measurement mode. The display indicating the present pulse waveform shown in FIG. 12 is displayed by pressing a PLS button 63a on the touch panel 63. The display indicating graphed sequential changes in the blood vessel evaluation information shown in FIG. 13 is displayed by pressing a V.I. button 63b on the touch panel 63. In this mode, pressing a button 64a with an icon corresponding to an event such as mealtime or administration of medicine displayed on the display section 54 on the touch panel allows the type of event to be stored in the event storage section 67 while being associated with the occurrence point. The measurement is terminated by pressing a "STOP" button 64b on the touch panel.

The manual measurement mode is selected by pressing the "MANUAL" button on the touch panel in the home mode. In the manual measurement mode, measurement intervals or time is previously set and the measurement is performed according to this setting. In this measurement mode, the display of the pulse waveform and the display of the graphed sequential changes in the blood vessel evaluation information can also be selected. Types of events such as mealtime or administration of medicine can be stored in the event storage section 67 while being associated with the occurrence point. The measurement can be terminated in the middle of the measurement by pressing the "STOP" button on the touch panel.

The data display mode is selected by pressing the "DATA" button on the touch panel in the home mode. In this mode, data to be displayed is selected from the data list previously recorded, and graphed sequential changes in the blood vessel evaluation information can be displayed as shown in FIG. 14, for example.

In this display, the presence of the event input by the event input section can be displayed using a specific symbol such as a small circle 66 as described above. When the cursor line 56 is positioned on the small circle 66, the type of event is displayed in the pop up window 57. The pulse rate and the changing rate of the blood vessel evaluation information at a point corresponding to the cursor line are displayed on the PLS and V.I. buttons 63a and 63b.

The subject's sex, birth date, and the like may be input in the data display mode on another screen. The structure for calculating the actual age from the birth date is the same as described in the modification example 3.4.1 of the embodiment A. In addition, the actual age may be input as illustrated in the embodiment A using FIG. 7 instead of inputting the birth date. In this case, the actual age calculation section 44 is not needed and data is directly input to the comparative analysis section 46 from the data input section 43.

4.4 Modification Example of Embodiment B 4.4.1

Each of the modification examples 3.4.2, 3.4.3, 3.4.4, 3.4.6, and 3.4.7 in the embodiment A is also applicable to the present embodiment.

4.4.2

The detection instruction section 51 need not allow the pulse wave sensor 18 and the waveform parameter calculation section 22 to detect at once at a time previously set, but may allow detection to be performed after confirming that there is little effect from body movement using an acceleration sensor, for example.

4.5 Effect of Embodiment B

According to the biological information evaluation apparatus 40 of the present embodiment, changes in the blood vessel evaluation information analyzed by the change analysis section 38 can be easily perceived by graphing on the display section 54. Moreover, changes in the blood vessel evaluation information can be perceived while associating the changes with the event which may affect the blood vessel evaluation information using the display of the display section 54.

5. Embodiment C

The embodiment C differs from the embodiment B in that an event detection section is used in place of the event input section, and an environment sensor section, a threshold value storage section, and a judgement section are additionally provided. In the following description, features differing from the embodiment B are mainly described. Other features are the same as in the embodiment B, and description of these features is omitted. In the drawings, corresponding sections are indicated using the same symbols.

5.1 External Structure of Biological Information Evaluation Apparatus

Figure 17:
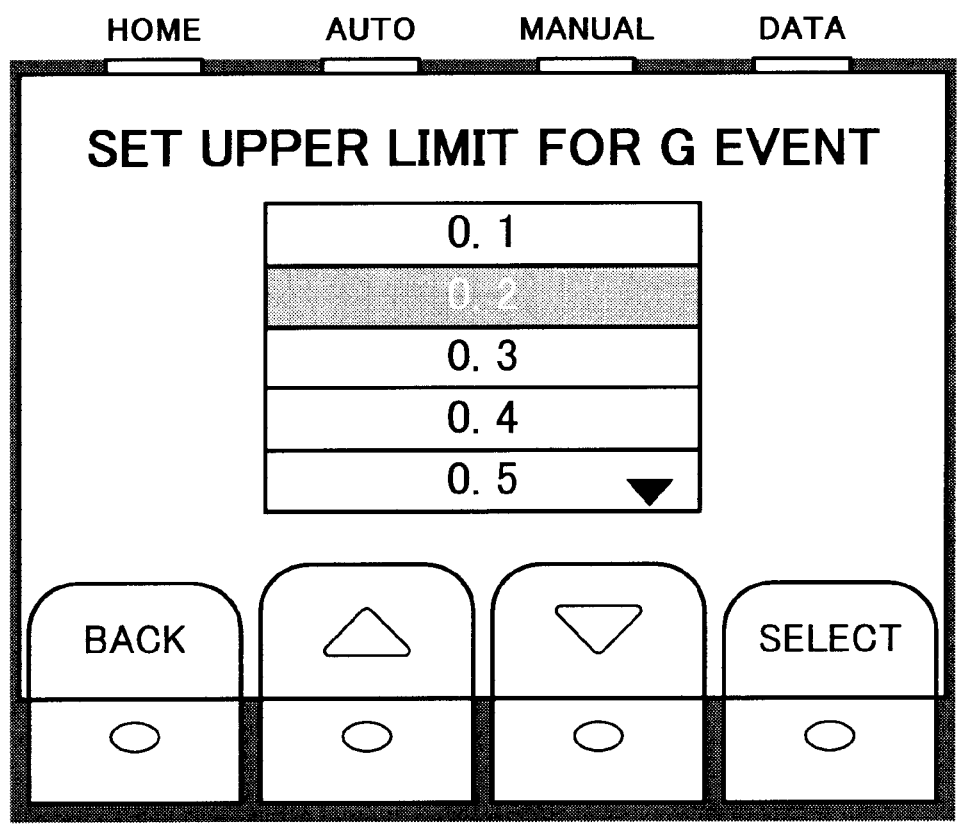
FIG. 17 is a view showing a display example of a display section of a biological information evaluation apparatus according to an embodiment C.
Figure 18:
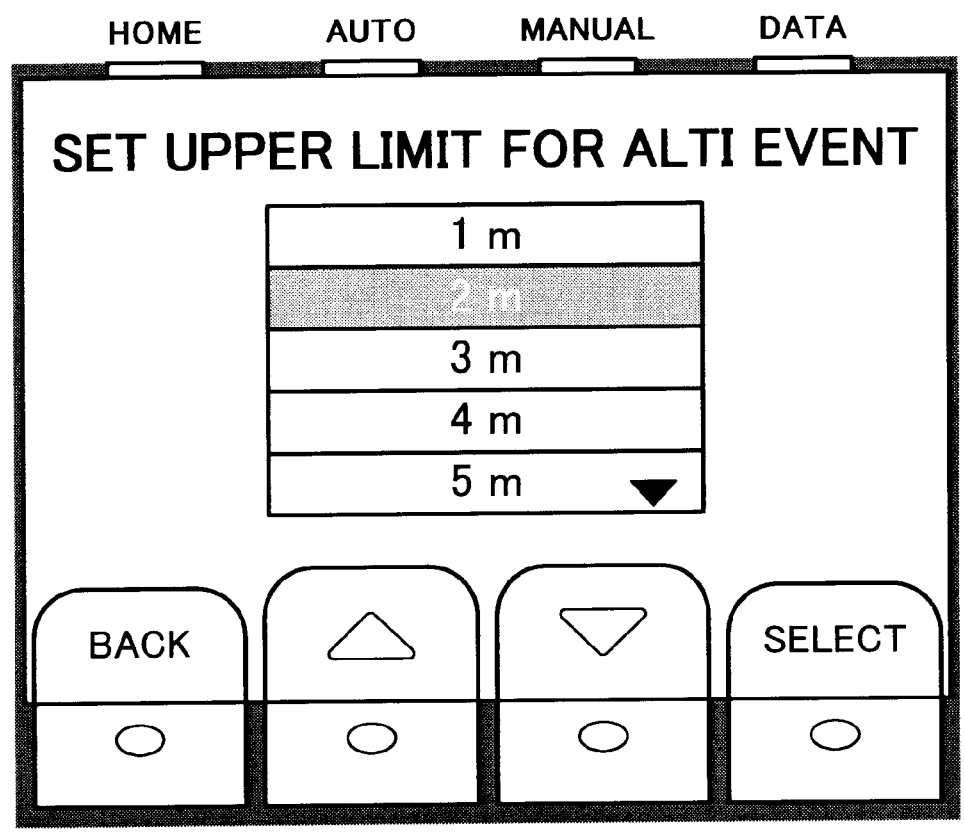
FIG. 18 is a view showing a display example of the display section of the biological information evaluation apparatus according to the embodiment C.
Figure 19:
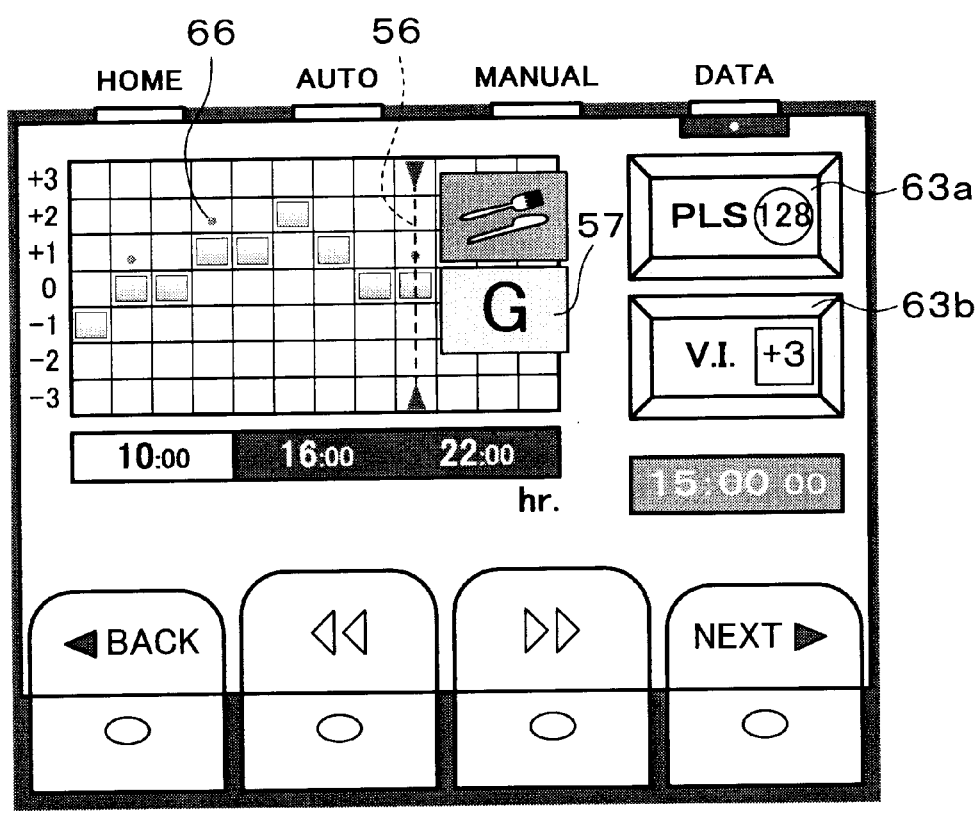
FIG. 19 is a view showing a display example of the display section of the biological information evaluation apparatus according to the embodiment C.

A biological information evaluation apparatus according to the present embodiment is externally formed in the same manner as the biological information evaluation apparatus of the embodiment B. FIGS. 17 to 19 are views showing display examples of the display section 54 as the notification section of the biological information evaluation apparatus of the present embodiment. Although not shown in the figures, the body section 62 or bands 58 in the present embodiment includes an environment sensor section having an environment sensor such as a thermosensor, humidity sensor, barometric pressure sensor, altitude sensor, or acceleration sensor.

5.2 Functional Structure of Biological Information Evaluation Apparatus

Figure 20:
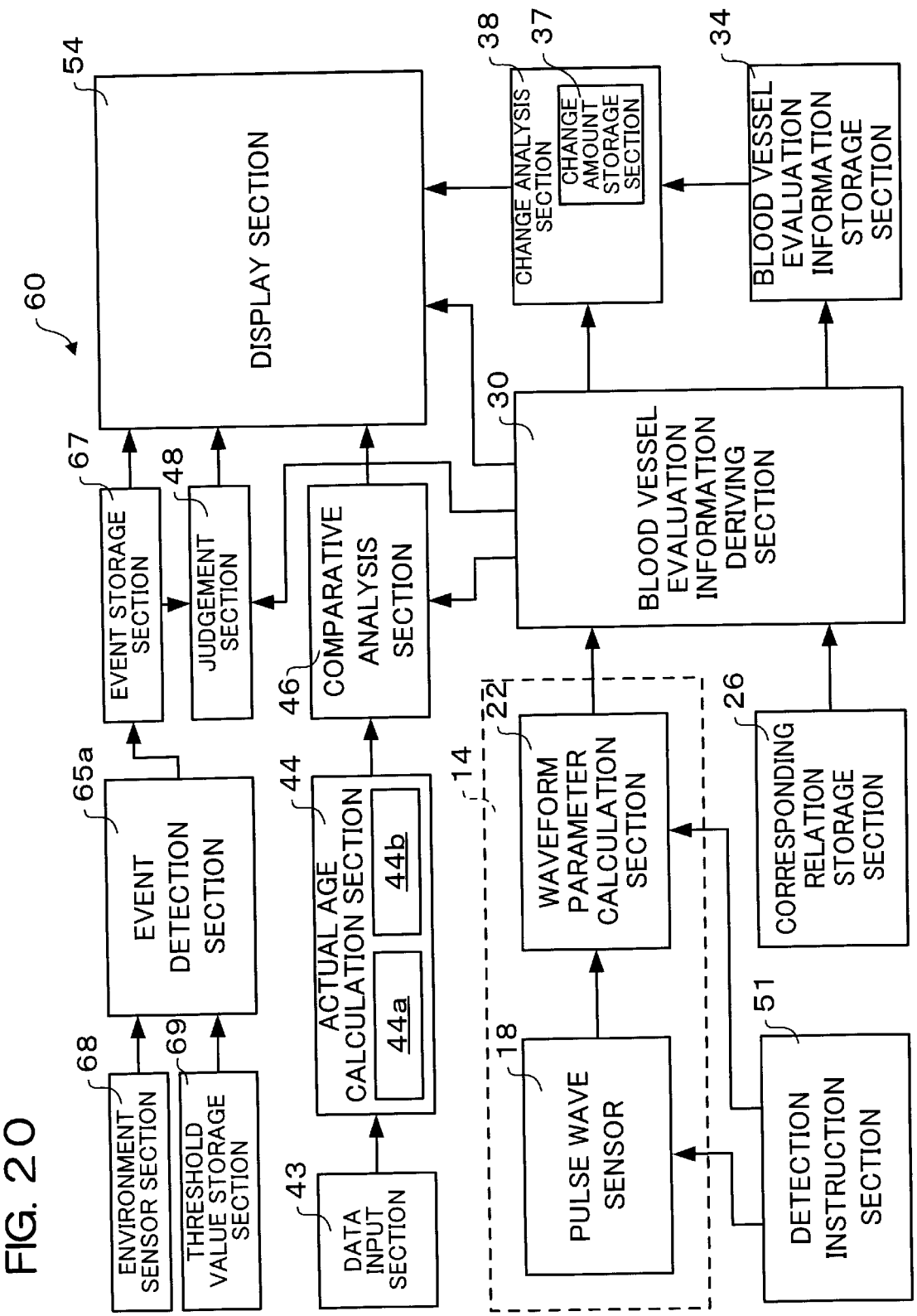
FIG. 20 is a block diagram showing the functional structure of the biological information evaluation apparatus according to the embodiment C.

FIG. 20 is a block diagram showing the functional structure of a biological information evaluation apparatus 60 according to the present embodiment. As shown in FIG. 20, the biological information evaluation apparatus 60 includes an environment sensor section 68 and a threshold value storage section 69 in addition to each block provided in the biological information evaluation apparatus 60 of the embodiment B. An event detection section 65a is used in place of the event input section 65.

The environment sensor section 68 includes at least one environment sensor for detecting environmental data which may affect the blood vessel evaluation information, such as a thermosensor, humidity sensor, barometric pressure sensor, altitude sensor, and acceleration sensor. The environment sensor section 68 further includes an amplifier section which amplifies signals from each sensor, and an A/D conversion section which converts the amplified signals into digital signals.

When the environmental data obtained by the environment sensor section 68 reaches a specified range, the event detection section 65a judges that the event may affect the blood vessel evaluation information. The event detection section 65a automatically detects the occurrence point and the type of the event and outputs them to the event storage section 67. Note that the term "environmental data reaches a specific range" includes not only the case where the numerical value of the environmental data reaches a range specified by two threshold values, but also the case where the numerical value of the environmental data exceeds the threshold value in a positive direction and the case where the numerical value of the environmental data exceeds the threshold value in a negative direction. Any of these cases is selected for each event. As examples of the types of events, a high temperature, low temperature, barometric pressure lower than a specific value, barometric pressure exceeding a specific value, altitude exceeding a specific value, acceleration within a specific range, acceleration exceeding a specific value, and the like can be given.

The threshold value storage section 69 stores threshold values for specifying a specific range for the environmental data to be detected by the event detection section 65 as an event corresponding to the type of the environmental data to be detected by the environment sensor section 68 and the type of the event. FIG. 17 shows a display example of the display section 54 as the notification section at the time of setting the upper limit for acceleration, which is one of two threshold values required for setting a specific range for acceleration so that the event detection section can automatically detect an event at which acceleration reaches the specific range. This display example illustrates the case of setting the upper limit for acceleration to 0.2 G. FIG. 18 shows a display example of the display section 54 as the notification section at the time of setting the upper limit for altitude, which is one of two threshold values required for setting a specified range for altitude so that the event detection section can automatically detect an event at which altitude reaches the specified range. This display example illustrates the case of setting the upper limit for altitude to 2 m. These settings allow the threshold value storage section 69 to store the threshold values for specifying a range for the environmental data to be detected by the event detection section 65 as an event.

The event storage section 67 stores the types of events detected by the event detection section 65a while associating the type with the occurrence point, and outputs the content to the display section 54.

The display section 54 of the present embodiment also displays information about the event detected by the event detection section 65a and stored in the event storage section 67. FIG. 19 shows a display example of the display section 54 in the data display mode. In the data display mode, the presence of the event detected by the event detection section 65a may be indicated using a specific symbol such as the small circle 66. When the cursor line 56 is positioned on the symbol indicating the presence of the event, the type of event is displayed in the pop up window 57. In this display example, the pop up window 57 showing "G" indicates that an event relating to acceleration occurred during that time period.

A judgement section 48 judges whether the change in the blood vessel evaluation information is either a psychogenic change or change accompanied by the environment or activities based on the type of event stored in the event storage section 67 while being associated with the occurrence point and the blood vessel evaluation information derived by the blood vessel evaluation information deriving section 30. Specifically, the judgement section 48 judges whether the functional change is either a psychogenic change or change accompanied by environmental conditions which cause hemodynamics to change such as a temperature, or activities such as exercise or labor. For example, in the case where the event storage section 67 has stored an event corresponding to acceleration within a specific range caused by walking or exercise which occurred before the change in the blood vessel evaluation information, the judgement section 48 judges that the change in the blood vessel evaluation information is accompanied by activities. The judgment results by the judgement section 48 are input into the display section 54 and displayed therein.

5.3 Operation of Biological Information Evaluation Apparatus

The operations of the biological information evaluation apparatus 60 are almost the same as those of the biological information evaluation apparatus 40 of the embodiment B. However, the operations relating to the environment sensor section 68 and the event detection section 65a and the operations relating to the judgement section 48 differ from the operations in the embodiment B.

In the biological information evaluation apparatus 60 of the present embodiment, the environment sensor section 68 detects continuously or at predetermined intervals at least one piece of environmental data which may affect the blood vessel evaluation information, such as temperature, humidity, barometric pressure, altitude, or acceleration in the auto-measurement mode or manual measurement mode.

When the environmental data obtained by the environment sensor section 68 reaches a specified range, the event detection section 65a judges that the event may affect the blood vessel evaluation information. The event detection section 65a automatically detects the occurrence point and the type of event, and outputs them to the event storage section 67. The event is stored in the event storage section 67 while being associated with the occurrence point.

In the data display mode, when data to be displayed is selected from the data list previously recorded, the graphed sequential changes in the blood vessel evaluation information are displayed as shown in FIG. 19, for example. In this display mode, the presence of the event detected by the event detection section is indicated using the small circle 66, for example. When the cursor line 56 is positioned on the small circle 66, the type of event is displayed in the pop up window 57.

In the data display mode, the judgement section 48 judges whether the change in the blood vessel evaluation information is either a psychogenic change or change accompanied by the environment or activities, based on the type of event stored in the event storage section 67 associated with the occurrence point and the blood vessel evaluation information derived by the blood vessel evaluation information deriving section 30. The judgment results are input to the display section 54 and displayed therein.

In addition, the threshold values stored in the threshold value storage section 69 can be set in the data display mode on another display screen. FIG. 17 shows a display example of the display section 54 at the time of setting one of two threshold values required for setting a specified range for acceleration so that the event detection section 65a can automatically detect an event at which acceleration reaches the specified range.

5.4 Modification Example of Embodiment C 5.4.1

Each of the modification examples 3.4.2, 3.4.3, 3.4.4, 3.4.6, and 3.4.7 in the embodiment A, and the modification example 4.4.2 in the embodiment B is also applicable to the present embodiment.

5.4.2

In the present embodiment, the biological information evaluation apparatus may include the event input section 65 described in the embodiment B.

5.5 Effect of Embodiment C

In addition to the effects of the embodiment B, the biological information evaluation apparatus 60 according to the present embodiment can recognize changes in the blood vessel evaluation information while associating the changes with an event which is automatically stored because the event may affect the blood vessel evaluation information. Moreover, it is possible to judge whether the change in the blood vessel evaluation information is either a psychogenic change or change accompanied by the environment or activities.

6. Embodiment D

The embodiment D differs from the embodiment A in that the waveform parameter detection section includes a blood pressure measurement section and a conversion section, the waveform parameter detection section detects the waveform parameter based on the blood pressure waveform, and the pulse wave sensor is a pressure sensor which detects fluid pressure, and also differs in the external structure. Other features are the same as in the embodiment A and the description of these features is omitted. In the drawings, corresponding sections are indicated using the same symbols.

6.1 Structure of Biological Information Evaluation Apparatus

Figure 21:
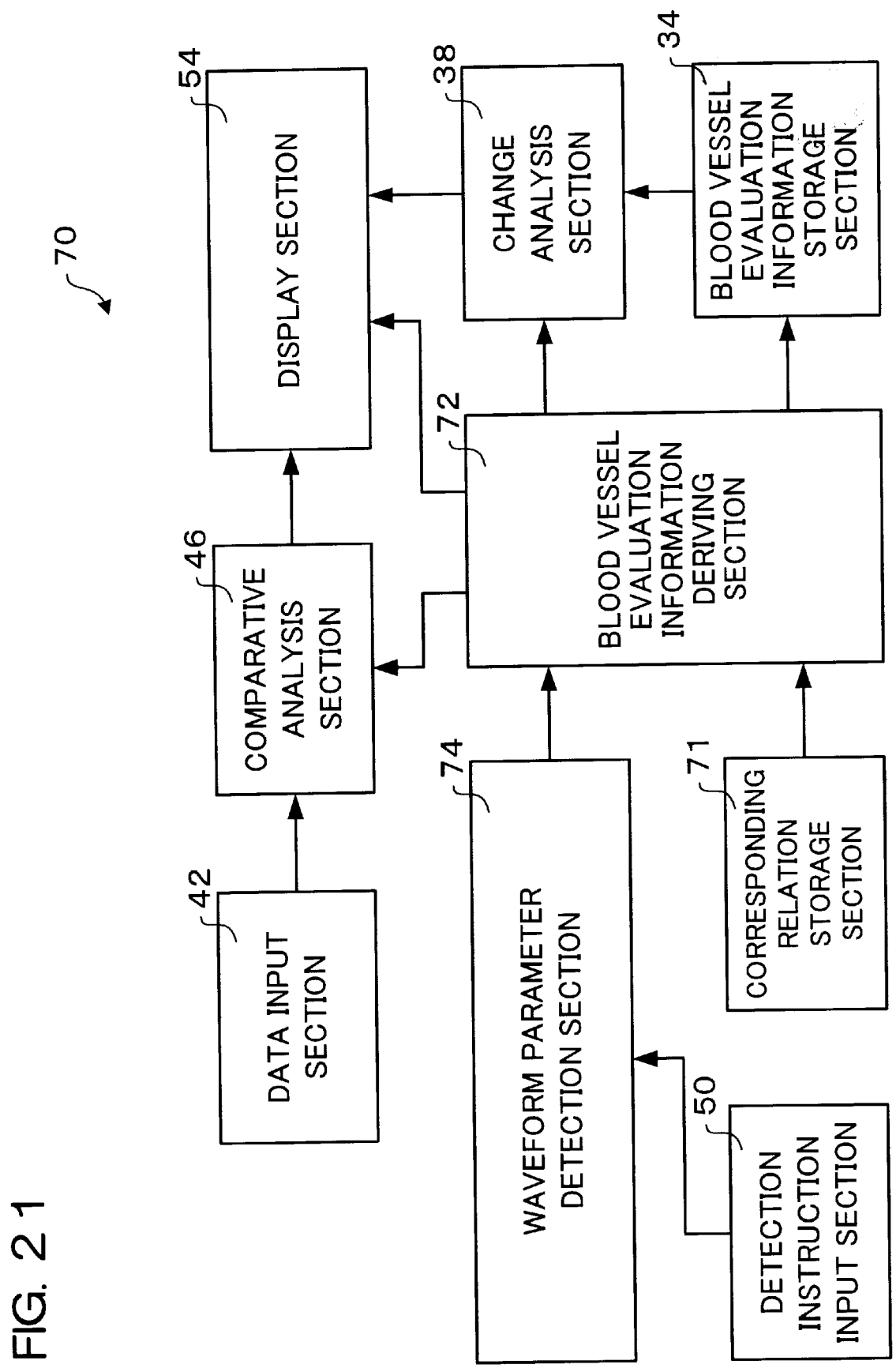
FIG. 21 is a block diagram showing the functional structure of the biological information evaluation apparatus according to the embodiment D.

FIG. 21 is a block diagram showing the functional structure of a biological information evaluation apparatus 70 according to the present embodiment. As shown in FIG. 21, the major difference in the functional structure between the biological information evaluation apparatus 70 and the embodiment A is that another waveform parameter detection section 74 is used in place of the waveform parameter detection section 14.

A corresponding relation storage section 71 of the biological information evaluation apparatus 70 stores the corresponding relation between the after-ejection pressure as the waveform parameter and the blood vessel evaluation information which is derived in advance.

A blood vessel evaluation information deriving section 72 of the biological information evaluation apparatus 70 derives the physiological age or degree of arteriosclerosis based on the after-ejection pressure detected by the waveform parameter detection section 74 and the corresponding relation stored in the corresponding relation storage section 71, specifically, the corresponding relation between the physiological age or degree of arteriosclerosis as the blood vessel evaluation information and the after-ejection pressure.

Figure 22:
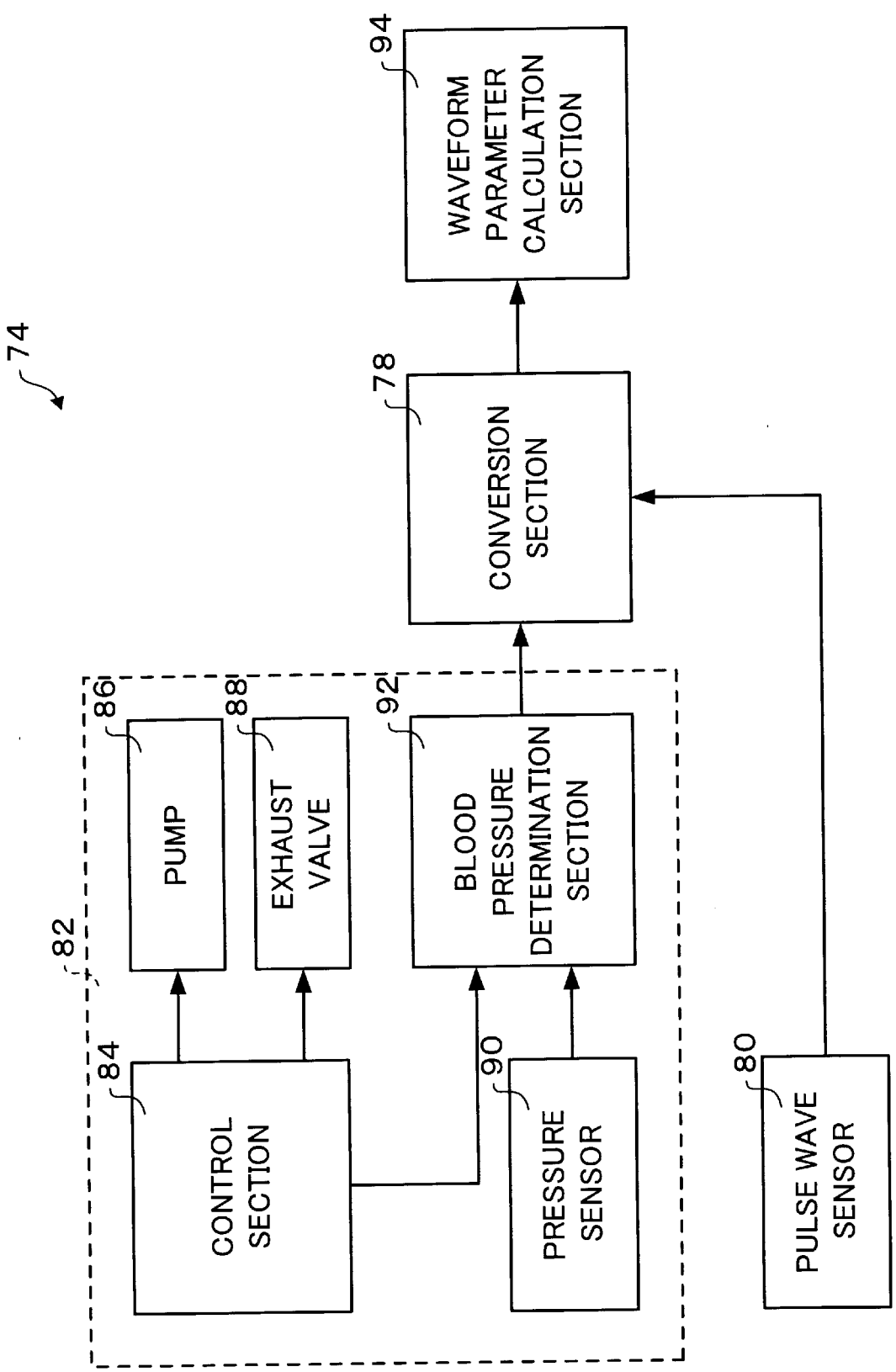
FIG. 22 is a block diagram showing the functional structure of the waveform parameter detection section shown in FIG. 21.

The waveform parameter detection section 74 includes a blood pressure measurement section 82, a pulse wave sensor 80, a conversion section 78, and a waveform parameter calculation section 94, as shown in FIG. 22 which is a block diagram showing the functional structure of the waveform parameter detection section 74. The blood pressure measurement section 82 measures the maximum blood pressure and the minimum blood pressure as described later in detail. The conversion section 78 converts the pulse waveform detected by the pulse wave sensor 80 into a blood pressure waveform based on the information about the maximum and minimum blood pressures measured by the blood pressure measurement section 82. The waveform parameter calculation section 94 calculates the waveform parameter such as the after-ejection pressure or dicrotic wave height based on the blood pressure waveform obtained by the conversion section 78.

The functional structure and operation of the biological information evaluation apparatus 70 are the same as those of the biological information evaluation apparatus 10 of the embodiment A except for the above-described features and the operations relating to the blood pressure measurement section 82 which makes up part of the waveform parameter detection section 74.

6.2 Structure of Blood Pressure Measurement Section

Figure 23:
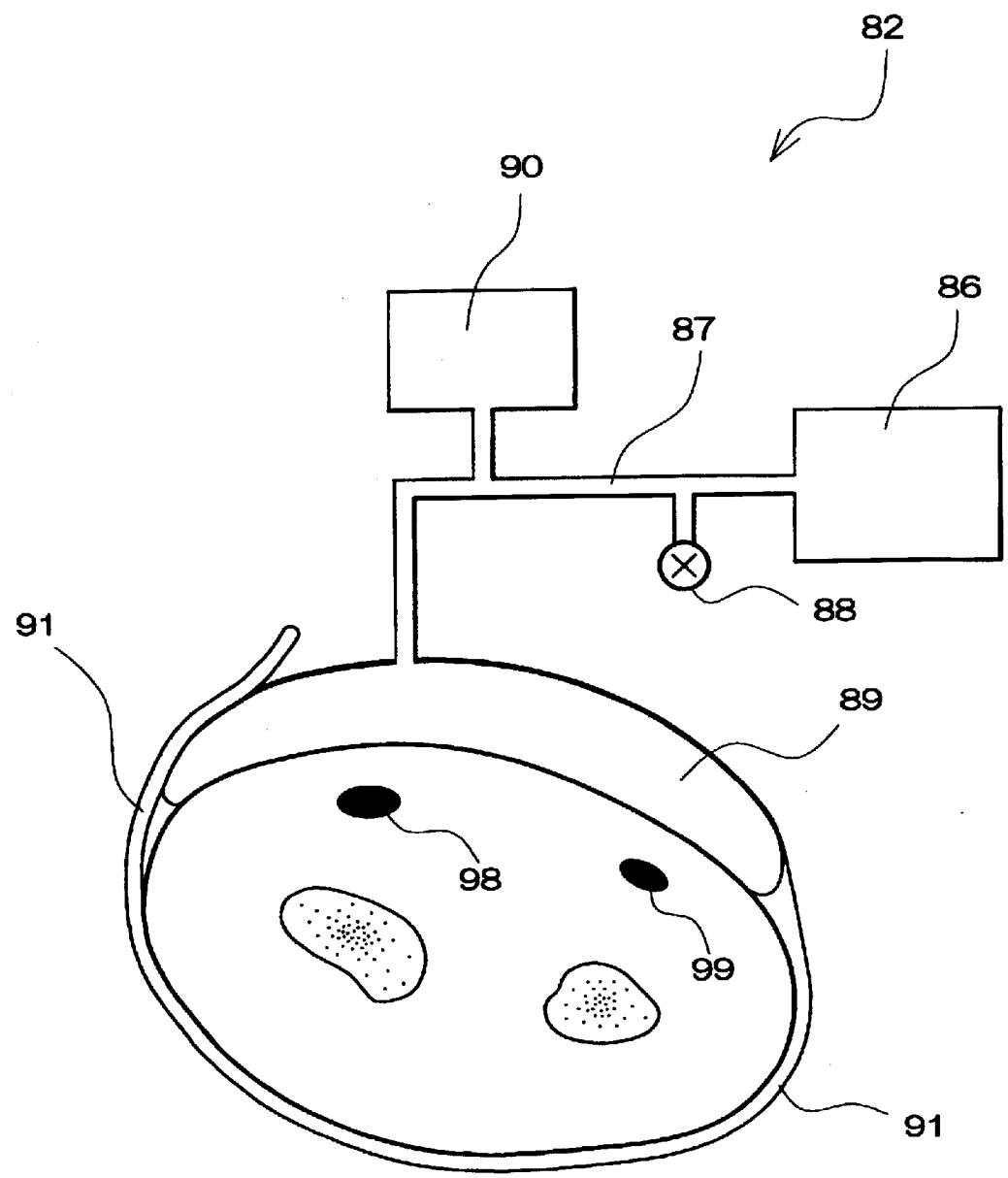
FIG. 23 is a view schematically showing a state of measuring blood pressure using a blood pressure measurement section worn on the wrist.

FIG. 23 is a view schematically showing a state of measuring the blood pressure using the blood pressure measurement section 82 which makes up part of the waveform parameter detection section 74 worn on the wrist. As shown in FIG. 23, the blood pressure measurement section 82 is formed so that the blood pressure can be measured with a cuff-like band 91 wound around the wrist. The band 91 includes a pressure applying section 89 in the shape of a bag on the inner side thereof. The band 91 is wound around the wrist so that the pressure applying section 89 is located so as to face the radial artery 98.

The pressure applying section 89 is formed in the shape of a bag to which a pump 86 and an exhaust valve 88 are connected through a tube 87. The volume of the pressure applying section 89 is controlled by adjusting the amount of fluid such as air, with which the pressure applying section 89 is filled, using the pump 86 and the exhaust valve 88, thereby controlling the pressure applied to the radial artery 98 and ulnar artery 99 by the pressure applying section 89. The pressure applying section 89 is large enough to be located above the radial artery 98 and ulnar artery 99 at the same time.

The tube 87 is equipped with a pressure sensor 90 which detects the pressure changes in the fluid. The pressure sensor 90 is formed so as to detect the vibration of the radial artery 98 which is transmitted as the pressure change in the fluid through the pressure applying section 89. Specifically, since the pressure applying section 89 located above the radial artery 98 is pressed corresponding to the vibration of the radial artery 98, the fluid pressure in the pressure applying section 89 changes according to the vibration of the radial artery 98. Therefore, the pressure sensor 90 which detects such a pressure change can output signals corresponding to the vibration of the radial artery 98. In the present embodiment, the pressure sensor 90 serves as the pulse wave sensor 80 in the waveform parameter detection section 74.

As shown in part of FIG. 22, the blood pressure measurement section 82 includes a control section 84 and a blood pressure determination section 92 in addition to each section as described above.

The control section 84 adjusts the amount of fluid with which the pressure applying section 89 is filled, by controlling the operation of the pump 86 and the exhaust valve 88. This causes the pressure applied by the pressure applying section 89 to change, thereby allowing the pressure applying section 89 to apply various levels of pressure to the radial artery 98 within a specific range. The control section 84 includes a CPU and a memory in which a program for operating the CPU is stored, for example.

The blood pressure determination section 92 takes information on the various levels of pressure applied by the pressure applying section 89 from the control section 84. The blood pressure determination section 92 determines the maximum and minimum blood pressures based on signals detected by the pressure sensor 90 at each of these pressure levels. The blood pressure determination section 92 includes a CPU and a memory in which a program for operating the CPU is stored, for example.

6.3 Operation of Blood Pressure Measurement Section

The blood pressure measurement section 82 measures blood pressure by operating as described below, for example.

The cuff-like band 91 is wound around the wrist so that the pressure applying section 89 is located at a position corresponding to the radial artery 98.

The control section 84 adjusts the amount of fluid with which the pressure applying section 89 is filled by controlling the pump 86 and the exhaust valve 88. This causes the pressure applied by the pressure applying section 89 to change, thereby allowing the pressure applying section 89 to apply various levels of pressure to the radial artery 98 within a specific range. Specifically, the pressure applied by the pressure applying section 89 is controlled by the control section 84 within a range exceeding commonly encountered blood pressures to some extent, for example, within a range of 250 to 20 mmHg.

The pressure sensor 90 which detects the vibration of the radial artery 98 detects signals corresponding to the vibration of the blood vessel wall due to blood flowing through the blood vessels constricted by the pressure applying section 89 at each pressure level applied by the pressure applying section 89. The results are stored in the blood pressure determination section 92 corresponding to each pressure level applied by the pressure applying section 89. Each pressure value applied by the pressure applying section 89 is transmitted to the blood pressure determination section 92 from the control section 84 which controls the pressure to be applied.

The blood pressure determination section 92 determines the blood pressure after a sufficient number of pressure samples are obtained over the above pressure range for the pressure applying section 89. Specifically, the blood pressure determination section 92 determines the highest pressure of the pressure applying section 89 detected by the pressure sensor 90 which detects the vibration due to blood flowing through the constricted blood vessels as the maximum blood pressure, and the lowest pressure of the pressure applying section 89 detected by the pressure sensor 90 which detects the vibration due to blood flowing through the constricted blood vessels as the minimum blood pressure. The principle of this blood pressure determination is the same as in a blood pressure measuring method in which the blood pressure is determined by monitoring the vibration of the blood vessel walls accompanied by blood flowing through the blood vessels at the peripheral side of the artery constricted by the pressure applied by the brachium band while changing the pressure applied to the brachium band (auscultation method).

6.4 Operation of Biological Information Evaluation Apparatus

The biological information evaluation apparatus 70 evaluates the blood vessels of the subject by operating as described below, for example.

The cuff-like band 91 is wound around the wrist so that the pressure applying section 89 in the blood pressure measurement section 82 is located at a position corresponding to the radial artery 98 as described above, thereby measuring the blood pressure.

The operations of the biological information evaluation apparatus thereafter are performed in a state for measuring the blood pressure using the blood pressure measurement section 82, specifically, in a state in which the cuff-like band 91 is wound around the wrist and the fluid is injected into the pressure applying section 89 so that a suitable pulse waveform is obtained by the pressure sensor 90. The pressure sensor 90 is used as the pulse wave sensor in place of the pulse wave sensor 18 in the embodiment A.

The operations of the biological information evaluation apparatus 70 are the same as those of the biological information evaluation apparatus 10 of the embodiment A except for the above features.

6.5 Modification Example of Embodiment D 6.5.1

The above description in the present embodiment illustrates an example in which the waveform parameter to be detected by the waveform parameter detection section 74 and used for the blood vessel evaluation information deriving section 72 to derive the blood vessel evaluation information is the after-ejection pressure. However, the waveform parameter to be detected by the waveform parameter detection section 74 and used for the blood vessel evaluation information deriving section 30 to derive the blood vessel evaluation information may be the dicrotic wave height. As described in "1. <Basic principle>", in the case of using the dicrotic wave height as the waveform parameter, the physiological age or degree of arteriosclerosis can also be derived as the blood vessel evaluation information.

6.5.2

The above description of the present embodiment illustrates an example in which the waveform parameter detection section 74 detects the waveform parameter when there is little effect from body movement by the instruction input into the detection instruction input section when there is little body movement. However, the waveform parameter detection section 74 maybe formed so as to continuously measure the pulse waveform and detect the waveform parameter based on the pulse waveform during a period in which body movement does not affect the pulse waveform. This enables the waveform parameter detection section 74 to detect an accurate waveform parameter without being affected by body movement. In this case, the detection instruction input section 50 may be omitted.

6.5.3

The above description of the present embodiment illustrates an example in which the radial artery 98 is the artery from which the pressure sensor 90 as the pulse wave sensor detects the vibration. However, the artery from which the pressure sensor 90 detects the pulse wave may be any artery in the extremities and fingers such as the ulnar artery at the wrist, the palmar digital artery which is an artery in the finger, the brachial artery at the upper arm, or the popliteal artery at the lower limbs.

6.5.4

As described in the modification example 3.4.2 in the embodiment A, a modification example provided with the change analysis section 39 including the basal blood vessel evaluation information deriving section 39*a* and the basal blood vessel evaluation information storage section 39*b* in place of the change analysis section 38 is also applicable to the present embodiment.

6.5.5

As illustrated in the embodiment B, the change analysis section 38 may include the change amount storage section 37, and the display section 54 may report the amount of change or changing rate at several points as numerical values or a graph. Moreover, as illustrated in the embodiment B, the event input section 65 for inputting an event which may affect the blood vessel evaluation information and the event storage section 67 for storing the type and the occurrence point of the event may be provided, and the display section 54 may display the type of event associated with the occurrence point.

6.5.6

As illustrated in the embodiment C, the biological information evaluation apparatus of the present embodiment may include the event detection section 65a which automatically inputs the environmental data detected by the environment sensor section 68 within a specific range as an event which may affect the blood vessel evaluation information, threshold value storage section 69, and event storage section 67. The biological information evaluation apparatus of the present embodiment may include the judgement section 48 as described in the embodiment C.

6.6 Effect of Embodiment D

As described above, in the biological information evaluation apparatus 70 according to the present embodiment, the corresponding relation between a specific waveform parameter in the blood pressure waveform and the blood vessel evaluation information is stored in advance in the corresponding relation storage section 71, and the blood vessel evaluation information deriving section 72 uniquely derives the blood vessel evaluation information by applying the detected waveform parameter to this corresponding relation. Therefore, the blood vessel evaluation information can be derived without the need for a large memory capacity or a large number of arithmetic operations.

The embodiments of the present invention are described above. However, the present invention is not limited to the above embodiments. Various modifications and variations are possible without departing from the spirit of the present invention and within the scope of the present invention.

What is claimed is:

1. A biological information evaluation apparatus comprising:
   a waveform parameter detection section which detects a specific waveform parameter based on a pulse waveform;
   a corresponding relation storage section which stores the corresponding relation between blood vessel evaluation information and the waveform parameter which is derived in advance; and
   a blood vessel evaluation information deriving section which derives the blood vessel evaluation information based on the waveform parameter detected by the waveform parameter detection section and the corresponding relation.

2. The biological information evaluation apparatus according to claim 1,
   wherein the waveform parameter detection section comprises a pulse wave sensor which detects the pulse waveform, and a waveform parameter calculation section which calculates the waveform parameter from the pulse waveform.

3. The biological information evaluation apparatus according to claim 1,
   wherein the waveform parameter detection section detects the waveform parameter when there is no effect of body movement.

4. The biological information evaluation apparatus according to claim 1, further comprising:
   a detection instruction input section into which an instruction for the waveform parameter detection section to start detection is input.

5. The biological information evaluation apparatus according to claim 1, further comprising:
   a notification section which notifies the pulse waveform or the blood vessel evaluation information.

6. The biological information evaluation apparatus according to claim 1,
   wherein the waveform parameter is a dicrotic wave height ratio which is a dicrotic wave height normalized by a pulse pressure, the dicrotic wave height being pressure difference between a blood pressure at a dicrotic notch and a blood pressure at a dicrotic wave peak, and pulse pressure being pressure difference between a maximum blood pressure and a minimum blood pressure.

7. A biological information evaluation apparatus comprising:
   a waveform parameter detection section which detects a specific waveform parameter based on a blood pressure waveform;
   a corresponding relation storage section which stores the corresponding relation between blood vessel evaluation information and the waveform parameter which is derived in advance; and
   a blood vessel evaluation information deriving section which derives the blood vessel evaluation information based on the waveform parameter detected by the waveform parameter detection section and the corresponding relation.

8. The biological information evaluation apparatus according to claim 7,
   wherein the waveform parameter detection section comprises a blood pressure measurement section which detects a maximum blood pressure and a minimum blood pressure, a pulse wave sensor which detects a pulse waveform, a conversion section which converts the pulse waveform into a blood pressure waveform, and a waveform parameter calculation section which calculates the waveform parameter from the blood pressure waveform.

9. The biological information evaluation apparatus according to claim 7,
   wherein the waveform parameter is a dicrotic wave height which is pressure difference between a blood pressure at a dicrotic notch and a blood pressure at a dicrotic wave peak.

10. The biological information evaluation apparatus according to claim 1, further comprising:
    a blood vessel evaluation information storage section which stores the blood vessel evaluation information; and
    a change analysis section which analyzes a change in the blood vessel evaluation information based on the blood vessel evaluation information derived by the blood vessel evaluation information deriving section and the blood vessel evaluation information stored in the blood vessel evaluation information storage section.

11. The biological information evaluation apparatus according to claim 10,
    wherein the change analysis section calculates the amount of change or changing rate of the blood vessel evaluation information relative to the blood vessel evaluation information at a specific point in time.

12. The biological information evaluation apparatus according to claim 11, further comprising:
- a change amount storage section which stores the amount of change or the changing rate calculated by the change analysis section; and
- a notification section which notifies the amount of change or the changing rate at several points in time stored in the change amount storage section.

13. The biological information evaluation apparatus according to claim 12,
- wherein the notification section notifies the amount of change or the changing rate at several points in time stored in the change amount storage section by means of a graph.

14. The biological information evaluation apparatus according to claim 12, further comprising:
- an event input section which inputs an occurrence point in time and type of event which is capable of affecting the blood vessel evaluation information; and
- an event storage section which stores the occurrence point in time and type of event,
- wherein the notification section notifies the type of event in association with the occurrence point in time.

15. The biological information evaluation apparatus according to claim 11, further comprising:
- an environment sensor section for detecting environmental data which is capable of affecting the blood vessel evaluation information;
- an event detection section which detects an occurrence point in time and type of event as an event which is capable of affecting the blood vessel evaluation information, when the environment data reaches a specific range;
- a threshold value storage section which stores a threshold value for specifying the specific range corresponding to a type of environmental data detected by the environment sensor section and a type of event; and
- an event storage section which stores the type and occurrence point in time of the event,
- wherein the notification section notifies the type of event in association with the occurrence point in time.

16. The biological information evaluation apparatus according to claim 1, further comprising:
- an event input section which inputs an occurrence point in time and type of event which is capable of affecting the blood vessel evaluation information; and
- an event storage section which stores the occurrence point in time and type of event.

17. The biological information evaluation apparatus according to claim 1, further comprising:
- an environment sensor section for detecting environmental data which is capable of affecting the blood vessel evaluation information;
- an event detection section which detects an occurrence point in time and type of event as an event which is capable of affecting the blood vessel evaluation information, when the environment data reaches a specific range;
- a threshold value storage section which stores a threshold value for specifying the specific range corresponding to a type of environmental data detected by the environment sensor section and a type of event; and
- an event storage section which stores the type and occurrence point in time of the event.

18. The biological information evaluation apparatus according to claim 17, further comprising:
- a judgement section which judges whether a change in the blood vessel evaluation information is either a psychogenic change or a change accompanied by an environment or an activity based on a type of event stored in the event storage section, in association with the occurrence point in time, and the blood vessel evaluation information derived by the blood vessel evaluation information deriving section.

19. The biological information evaluation apparatus according to claim 10,
- wherein the change analysis section comprises a basal blood vessel evaluation information deriving section which derives the blood vessel evaluation information when the basal metabolism of a subject is in a lowest region during a specific period of time based on the blood vessel evaluation information stored in the blood vessel evaluation information storage section, and a basal blood vessel evaluation information storage section which stores the basal blood vessel evaluation information derived by the basal blood vessel evaluation information deriving section, and
- wherein the change analysis section analyzes changes in the blood vessel evaluation information based on the blood vessel evaluation information derived by the blood vessel evaluation information deriving section and the basal blood vessel evaluation information stored in the basal blood vessel evaluation information storage section.

20. The biological information evaluation apparatus according to claim 10, further comprising:
- a notification section which notifies an analysis result in the change analysis section.

21. The biological information evaluation apparatus according to claim 1, further comprising:
- a blood vessel evaluation information storage section which stores the blood vessel evaluation information; and
- a basal blood vessel evaluation information deriving section which derives the blood vessel evaluation information when the basal metabolism of a subject is in a lowest region during a specific period of time based on the blood vessel evaluation information stored in the blood vessel evaluation information storage section.

22. The biological information evaluation apparatus according to claim 1,
- wherein the blood vessel evaluation information is a physiological age of a blood vessel.

23. The biological information evaluation apparatus according to claim 22, further comprising:
- a data input section into which an actual age of a subject is input; and
- a comparative analysis section which compares and analyzes the physiological age of the blood vessel based on the physiological age of the blood vessel derived by the blood vessel evaluation information deriving section and the actual age.

24. The biological information evaluation apparatus according to claim 23, further comprising:
- a notification section which notifies an analysis result in the comparative analysis section.

25. The biological information evaluation apparatus according to claim 22, further comprising:
- a data input section into which a birth date of a subject is input;

an actual age calculation section which calculates an actual age of the subject based on the birth date of the subject input into the data input section; and a comparative analysis section which compares and analyzes the physiological age of a blood vessel based on the physiological age of the blood vessel derived by the blood vessel evaluation information deriving section and the actual age, wherein the actual age calculation section comprises a birth date storage section which stores the birth date of the subject input into the data input section, and a present date calculation section which calculates a present date, and calculates the actual age of the subject based on the birth date of the subject stored in the birth date storage section and the present date calculated in the present date calculation section.

26. The biological information evaluation apparatus according to claim 1, wherein the blood vessel evaluation information is a degree of arteriosclerosis of a blood vessel.

27. The biological information evaluation apparatus according to claim 26, further comprising:

a data input section into which a birth date of a subject is input;

an actual age calculation section which calculates an actual age of the subject based on the birth date of the subject input into the data input section; and a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age, wherein the actual age calculation section comprises a birth date storage section which stores the birth date of the subject input into the data input section, and a present date calculation section which calculates a present date, and calculates the actual age of the subject based on the birth date of the subject stored in the birth date storage section and the present date calculated in the present date calculation section.

* * * * *

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 29,
Line 41, please change Claim 1 to read:

1. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section; and
    a blood vessel evaluation information deriving section which derives the blood vessel evaluation information based on the waveform parameter detected by the waveform parameter detection section and the corresponding relation, and
    wherein the waveform parameter is an after-ejection pressure ratio that is an after-ejection pressure normalized by a pulse pressure, the after-ejection pressure being a pressure difference between a blood pressure at a dicrotic notch and a maximum pressure, and the pulse pressure being a pressure difference between the maximum blood pressure and a minimum blood pressure.

Column 30,
Line 6, please change Claim 5 to read:

5. The biological information evaluation apparatus according to claim 1, further comprising:
    a notification section that provides a notification of the pulse waveform or the blood vessel evaluation information.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 30 (cont'd),
Line 10, please change Claim 6 to read:

6. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section; and a blood vessel evaluation information deriving section which derives the blood vessel evaluation information based on the waveform parameter detected by the waveform parameter detection section and the corresponding relation, and wherein the waveform parameter is a dicrotic wave height ratio which is a dicrotic wave height normalized by a pulse pressure, the dicrotic wave height being a pressure difference between a blood pressure at a dicrotic notch and a blood pressure at a dicrotic wave peak, and the pulse pressure being a pressure difference between a maximum blood pressure and a minimum blood pressure.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 30 (cont'd),</u>
Line 19, please change Claim 7 to read:

7. A biological information evaluation apparatus comprising:

a waveform parameter detection section which detects a specific waveform parameter based on a blood pressure waveform;

a corresponding relation storage section which stores the corresponding relation between blood vessel evaluation information and a waveform parameter which is derived in advance of detection of the specific waveform parameter by the waveform parameter detection section; and a blood vessel evaluation information deriving section which derives the blood vessel evaluation information based on the waveform parameter detected by the waveform parameter detection section and the corresponding relation, and wherein the waveform parameter is an after-ejection pressure which is a pressure difference between a blood pressure at a dicrotic notch and a maximum blood pressure.

UNITED STATES PATENT AND TRADEMARK OFFICE
CERTIFICATE OF CORRECTION

PATENT NO.      : 6,592,528 B2
DATED           : July 15, 2003
INVENTOR(S)     : Kazuhiko Amano It is certified that error appears in the above-identified patent and that said Letters Patent is hereby corrected as shown below:

Column 30 (cont'd),
Line 44, please change Claim 9 to read:

9.  A biological information evaluation apparatus comprising:
     a waveform parameter detection section which detects a specific waveform parameter based on a blood pressure waveform;
     a corresponding relation storage section which stores the corresponding relation between blood vessel evaluation information and a waveform parameter which is derived in advance of detection of the specific waveform parameter by the waveform parameter detection section; and
     a blood vessel evaluation information deriving section which derives the blood vessel evaluation information based on the waveform parameter detected by the waveform parameter detection section and the corresponding relation, and
     wherein the waveform parameter is a dicrotic wave height which is a pressure difference between a blood pressure at a dicrotic notch and a blood pressure at a dicrotic wave peak.

UNITED STATES PATENT AND TRADEMARK OFFICE
CERTIFICATE OF CORRECTION

PATENT NO.    : 6,592,528 B2
DATED         : July 15, 2003
INVENTOR(S)   : Kazuhiko Amano It is certified that error appears in the above-identified patent and that said Letters Patent is hereby corrected as shown below:

<u>Column 31,</u>
Line 42, please change Claim 16 to read:

16. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

an event input section which inputs an occurrence point in time and type of event which is capable of affecting the blood vessel evaluation information; and an event storage section which stores the occurrence point in time and type of event.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 31,
Line 49, please change Claim 17 to read:

17. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

an environment sensor section for detecting environmental data which is capable of affecting the blood vessel evaluation information;

an event detection section which detects an occurrence point in time and type of event as an event which is capable of affecting the blood vessel evaluation information, when the environment data reaches a specific range;

a threshold value storage section which stores a threshold value for specifying the specific range corresponding to a type of environmental data detected by the environment sensor section and a type of event; and an event storage section which stores the type and occurrence point in time of the event.

UNITED STATES PATENT AND TRADEMARK OFFICE
CERTIFICATE OF CORRECTION

PATENT NO.     : 6,592,528 B2
DATED          : July 15, 2003
INVENTOR(S)    : Kazuhiko Amano It is certified that error appears in the above-identified patent and that said Letters Patent is hereby corrected as shown below:

Column 32,
Line 31, please change Claim 20 to read:

20. The biological information evaluation apparatus according to claim 10, further comprising:
    a notification section that provides a notification of an analysis result in the change analysis section.

Line 35, please change Claim 21 to read:

21. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    a blood vessel evaluation information storage section which stores the blood vessel evaluation information; and
    a basal blood vessel evaluation information deriving section which derives the blood vessel evaluation information when the basal metabolism of a subject is in a lowest region during a specific period of time based on the blood vessel evaluation information stored in the blood vessel evaluation information storage section.

Column 32,
Line 46, please change Claim 22 to read:

22. A biological information evaluation apparatus comprising:
    a waveform parameter detection section which detects a specific waveform parameter based on a pulse waveform;

UNITED STATES PATENT AND TRADEMARK OFFICE
CERTIFICATE OF CORRECTION

PATENT NO.      : 6,592,528 B2
DATED           : July 15, 2003
INVENTOR(S)     : Kazuhiko Amano It is certified that error appears in the above-identified patent and that said Letters Patent is hereby corrected as shown below:

Column 32, (cont'd)

a corresponding relation storage section which stores the corresponding relation between blood vessel evaluation information and a waveform parameter which is derived in advance of detection of the specific waveform parameter by the waveform parameter detection section; and a blood vessel evaluation information deriving section which derives the blood vessel evaluation information based on the waveform parameter detected by the waveform parameter detection section and the corresponding relation; and wherein the blood vessel evaluation information is a physiological age of a blood vessel.

Column 32,
Line 59, please change Claim 24 to read:

24. The biological information evaluation apparatus according to claim 23, further comprising:

a notification section that provides a notification of an analysis result in the comparative analysis section.

Column 33,
Line 17, please change Claim 26 to read:

26. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

a data input section into which an actual age of a subject is input; and

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 33, (cont'd)

a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age; and wherein the blood vessel evaluation information is a degree of arteriosclerosis of a blood vessel.

Column 33,
Line 21, please change Claim 27 to read:

27. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 33, (cont'd)

a data input section into which a birth date of a subject is input;
    an actual age calculation section which calculates an actual age of the subject based on the birth date of the subject input into the data input section; and
    a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age,
    wherein the actual age calculation section comprises a birth date storage section which stores the birth date of the subject input into the data input section, and a present date calculation section which calculates a present date, and calculates the actual age of the subject based on the birth date of the subject stored in the birth date storage section and the present date calculated in the present date calculation section, and
    wherein the blood vessel evaluation information is a degree of arteriosclerosis of a blood vessel.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,592,528 B2
DATED          : July 15, 2003
INVENTOR(S)    : Kazuhiko Amano It is certified that error appears in the above-identified patent and that said Letters Patent is hereby corrected as shown below:

Column 29,
Line 41, please change Claim 1 to read:

1. A biological information evaluation apparatus comprising:
   a waveform parameter detection section which detects a specific waveform parameter based on a pulse waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation, and
   wherein the waveform parameter is an after-ejection pressure ratio that is an after-ejection pressure normalized by a pulse pressure, the after-ejection pressure being a pressure difference between a blood pressure at a dicrotic notch and a maximum pressure, and the pulse pressure being a pressure difference between the maximum blood pressure and a minimum blood pressure.

Column 30,
Line 6, please change Claim 5 to read:

5. The biological information evaluation apparatus according to claim 1, further comprising:
   a notification section that provides a notification of the pulse waveform or the blood vessel evaluation information.

UNITED STATES PATENT AND TRADEMARK OFFICE
CERTIFICATE OF CORRECTION

PATENT NO.     : 6,592,528 B2
DATED          : July 15, 2003
INVENTOR(S)    : Kazuhiko Amano It is certified that error appears in the above-identified patent and that said Letters Patent is hereby corrected as shown below:

Column 30 (cont'd),
Line 10, please change Claim 6 to read:

6. A biological information evaluation apparatus comprising:
   a waveform parameter detection section which detects a specific waveform parameter based on a pulse waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation, and
   wherein the waveform parameter is a dicrotic wave height ratio which is a dicrotic wave height normalized by a pulse pressure, the dicrotic wave height being a pressure difference between a blood pressure at a dicrotic notch and a blood pressure at a dicrotic wave peak, and the pulse pressure being a pressure difference between a maximum blood pressure and a minimum blood pressure.

Line 19, please change Claim 7 to read:

7. A biological information evaluation apparatus comprising:
   a waveform parameter detection section which detects a specific waveform parameter based on a blood pressure waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation, and
   wherein the waveform parameter is an after-ejection pressure which is a pressure difference between a blood pressure at a dicrotic notch and a maximum blood pressure.

UNITED STATES PATENT AND TRADEMARK OFFICE
CERTIFICATE OF CORRECTION

PATENT NO.      : 6,592,528 B2
DATED           : July 15, 2003
INVENTOR(S)     : Kazuhiko Amano It is certified that error appears in the above-identified patent and that said Letters Patent is hereby corrected as shown below:

Column 30 (cont'd),
Line 44, please change Claim 9 to read:

9. A biological information evaluation apparatus comprising:
   a waveform parameter detection section which detects a specific waveform parameter based on a blood pressure waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation, and
   wherein the waveform parameter is a dicrotic wave height which is a pressure difference between a blood pressure at a dicrotic notch and a blood pressure at a dicrotic wave peak.

Line 50, please change Claim 10 to read:

10. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    a blood vessel evaluation information storage section which stores the blood vessel evaluation information; and
    a change analysis section which analyzes a change in the blood vessel evaluation information based on the blood vessel evaluation information derived by the blood vessel evaluation information deriving section and the blood vessel evaluation information stored in the blood vessel evaluation information storage section.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 31,</u>
Line 1, please change Claim 12 to read:

12. The biological information evaluation apparatus according to claim 11, further comprising:
    a change amount storage section which stores the amount of change or the changing rate calculated by the change analysis section; and
    a notification section that provides a notification of the amount of change or the changing rate at several points in time stored in the change amount storage section.

Line 9, please change Claim 13 to read:

13. The biological information evaluation apparatus according to claim 12,
    wherein the notification section provides a notification of the amount of change or the changing rate at several points in time stored in the change amount storage section using a graph.

Line 15, please change Claim 14 to read:

14. The biological information evaluation apparatus according to claim 12, further comprising:
    an event input section which inputs an occurrence point in time and type of event which is capable of affecting the blood vessel evaluation information; and
    an event storage section which stores the occurrence point in time and type of event,
    wherein the notification section provides a notification of the type of event in association with the occurrence point in time.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 31,</u>
Line 24, please change Claim 15 to read:

15. The biological information evaluation apparatus according to claim 11, furth comprising:

an environment sensor section for detecting environmental data which is capable of affecting the blood vessel evaluation information;

an event detection section which detects an occurrence point in time and  event as an event which is capable of affecting the blood vessel evaluation inform when the environment data reaches a specific range;

a threshold value storage section which stores a threshold value for speci the specific range corresponding to a type of environmental data detected by the environment sensor section and a type of event; and an event storage section which stores the type and occurrence point in tin the event, wherein the notification section provides a notification of the type of even association with the occurrence point in time.

Line 42, please change Claim 16 to read:

16. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

an event input section which inputs an occurrence point in time and type of event which is capable of affecting the blood vessel evaluation information; and an event storage section which stores the occurrence point in time and type of event.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 31,
Line 49, please change Claim 17 to read:

17. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    an environment sensor section for detecting environmental data which is capable of affecting the blood vessel evaluation information;
    an event detection section which detects an occurrence point in time and type of event as an event which is capable of affecting the blood vessel evaluation information, when the environment data reaches a specific range;
    a threshold value storage section which stores a threshold value for specifying the specific range corresponding to a type of environmental data detected by the environment sensor section and a type of event; and
    an event storage section which stores the type and occurrence point in time of the event.

Column 32,
Line 31, please change Claim 20 to read:

20. The biological information evaluation apparatus according to claim 10, further comprising:
    a notification section that provides a notification of an analysis result in the change analysis section.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 32, cont'd.,
Line 35, please change Claim 21 to read:

21. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    a blood vessel evaluation information storage section which stores the blood vessel evaluation information; and
    a basal blood vessel evaluation information deriving section which derives the blood vessel evaluation information when the basal metabolism of a subject is in a lowest region during a specific period of time based on the blood vessel evaluation information stored in the blood vessel evaluation information storage section.

Line 46, please change Claim 22 to read:

22. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section; and
    a blood vessel evaluation information deriving section which derives the blood vessel evaluation information based on the waveform parameter detected by the waveform parameter detection section and the corresponding relation; and
    wherein the blood vessel evaluation information is a physiological age of a blood vessel.

UNITED STATES PATENT AND TRADEMARK OFFICE
CERTIFICATE OF CORRECTION

PATENT NO.    : 6,592,528 B2
DATED         : July 15, 2003
INVENTOR(S)   : Kazuhiko Amano It is certified that error appears in the above-identified patent and that said Letters Patent is hereby corrected as shown below:

Column 32, cont'd.,
Line 59, please change Claim 24 to read:

24. The biological information evaluation apparatus according to claim 23, further comprising:
   a notification section that provides a notification of an analysis result in the comparative analysis section.

Column 33,
Line 17, please change Claim 26 to read:

26. A biological information evaluation apparatus comprising:
   a waveform parameter detection section which detects a specific waveform parameter based on a pulse waveform;
   a corresponding relation storage section which stores the corresponding relation between blood vessel evaluation information and a waveform parameter which is derived in advance of detection of the specific waveform parameter by the waveform parameter detection section;
   a blood vessel evaluation information deriving section which derives the blood vessel evaluation information based on the waveform parameter detected by the waveform parameter detection section and the corresponding relation;
   a data input section into which an actual age of a subject is input; and
   a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age; and
   wherein the blood vessel evaluation information is a degree of arteriosclerosis of a blood vessel.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 33,</u>
Line 21, please change Claim 27 to read:

> 27. A biological information evaluation apparatus comprising:
>
> a waveform parameter detection section which detects a specific waveform parameter based on a pulse waveform;
>
> a corresponding relation storage section which stores the corresponding relation between blood vessel evaluation information and a waveform parameter which is derived in advance of detection of the specific waveform parameter by the waveform parameter detection section;
>
> a blood vessel evaluation information deriving section which derives the blood vessel evaluation information based on the waveform parameter detected by the waveform parameter detection section and the corresponding relation;
>
> a data input section into which a birth date of a subject is input;
>
> an actual age calculation section which calculates an actual age of the subject based on the birth date of the subject input into the data input section; and
>
> a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age,
>
> wherein the actual age calculation section comprises a birth date storage section which stores the birth date of the subject input into the data input section, and a present date calculation section which calculates a present date, and calculates the actual age of the subject based on the birth date of the subject stored in the birth date storage section and the present date calculated in the present date calculation section, and
>
> wherein the blood vessel evaluation information is a degree of arteriosclerosis of a blood vessel.

This certificate supersedes Certificate of Correction issued August 17, 2004.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO.     : 6,592,528 B2
DATED          : July 15, 2003
INVENTOR(S)    : Kazuhiko Amano It is certified that error appears in the above-identified patent and that said Letters Patent is hereby corrected as shown below:

Column 29,
Line 41, please change Claim 1 to read:

1. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section; and
    a blood vessel evaluation information deriving section which derives the blood vessel evaluation information based on the waveform parameter detected by the waveform parameter detection section and the corresponding relation, and
    wherein the waveform parameter is an after-ejection pressure ratio that is an after-ejection pressure normalized by a pulse pressure, the after-ejection pressure being a pressure difference between a blood pressure at a dicrotic notch and a maximum pressure, and the pulse pressure being a pressure difference between the maximum blood pressure and a minimum blood pressure.

Column 30,
Line 6, please change Claim 5 to read:

5. The biological information evaluation apparatus according to claim 1, further comprising:
    a notification section that provides a notification of the pulse waveform or the blood vessel evaluation information.

UNITED STATES PATENT AND TRADEMARK OFFICE
CERTIFICATE OF CORRECTION

PATENT NO.     : 6,592,528 B2
DATED          : July 15, 2003
INVENTOR(S)    : Kazuhiko Amano It is certified that error appears in the above-identified patent and that said Letters Patent is hereby corrected as shown below:

Column 30 (cont'd),
Line 10, please change Claim 6 to read:

6. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section; and
    a blood vessel evaluation information deriving section which derives the blood vessel evaluation information based on the waveform parameter detected by the waveform parameter detection section and the corresponding relation, and
    wherein the waveform parameter is a dicrotic wave height ratio which is a dicrotic wave height normalized by a pulse pressure, the dicrotic wave height being a pressure difference between a blood pressure at a dicrotic notch and a blood pressure at a dicrotic wave peak, and the pulse pressure being a pressure difference between a maximum blood pressure and a minimum blood pressure.

Line 19, please change Claim 7 to read:

7. A biological information evaluation apparatus comprising:
    a waveform parameter detection section which detects a specific waveform parameter based on a blood pressure waveform;
    a corresponding relation storage section which stores the corresponding relation between blood vessel evaluation information and a waveform parameter which is derived in advance of detection of the specific waveform parameter by the waveform parameter detection section; and
    a blood vessel evaluation information deriving section which derives the blood vessel evaluation information based on the waveform parameter detected by the waveform parameter detection section and the corresponding relation, and
    wherein the waveform parameter is an after-ejection pressure which is a pressure difference between a blood pressure at a dicrotic notch and a maximum blood pressure.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 30 (cont'd),
Line 44, please change Claim 9 to read:

9. A biological information evaluation apparatus comprising:
   a waveform parameter detection section which detects a specific waveform parameter based on a blood pressure waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation, and
   wherein the waveform parameter is a dicrotic wave height which is a pressure difference between a blood pressure at a dicrotic notch and a blood pressure at a dicrotic wave peak.

Line 50, please change Claim 10 to read:

10. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    a blood vessel evaluation information storage section which stores the blood vessel evaluation information; and
    a change analysis section which analyzes a change in the blood vessel evaluation information based on the blood vessel evaluation information derived by the blood vessel evaluation information deriving section and the blood vessel evaluation information stored in the blood vessel evaluation information storage section.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 31,</u>
Line 1, please change Claim 12 to read:

12. The biological information evaluation apparatus according to claim 11, further comprising:
    a change amount storage section which stores the amount of change or the changing rate calculated by the change analysis section; and
    a notification section that provides a notification of the amount of change or the changing rate at several points in time stored in the change amount storage section.

Line 9, please change Claim 13 to read:

13. The biological information evaluation apparatus according to claim 12,
    wherein the notification section provides a notification of the amount of change or the changing rate at several points in time stored in the change amount storage section using a graph.

Line 15, please change Claim 14 to read:

14. The biological information evaluation apparatus according to claim 12, further comprising:
    an event input section which inputs an occurrence point in time and type of event which is capable of affecting the blood vessel evaluation information; and
    an event storage section which stores the occurrence point in time and type of event,
    wherein the notification section provides a notification of the type of event in association with the occurrence point in time.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 31,
Line 24, please change Claim 15 to read:

15. The biological information evaluation apparatus according to claim 11, further comprising:
    an environment sensor section for detecting environmental data which is capable of affecting the blood vessel evaluation information;
    an event detection section which detects an occurrence point in time and type of event as an event which is capable of affecting the blood vessel evaluation information, when the environment data reaches a specific range;
    a threshold value storage section which stores a threshold value for specifying the specific range corresponding to a type of environmental data detected by the environment sensor section and a type of event; and
    an event storage section which stores the type and occurrence point in time of the event,
    wherein the notification section provides a notification of the type of event in association with the occurrence point in time.

Line 42, please change Claim 16 to read:

16. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    an event input section which inputs an occurrence point in time and type of event which is capable of affecting the blood vessel evaluation information; and
    an event storage section which stores the occurrence point in time and type of event.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

<u>Column 31,</u>
Line 49, please change Claim 17 to read:

17. A biological information evaluation apparatus comprising:
 a waveform parameter detection section which detects a specific waveform parameter based on a pulse waveform;
 a corresponding relation storage section which stores the corresponding relation between blood vessel evaluation information and a waveform parameter which is derived in advance of detection of the specific waveform parameter by the waveform parameter detection section;
 a blood vessel evaluation information deriving section which derives the blood vessel evaluation information based on the waveform parameter detected by the waveform parameter detection section and the corresponding relation;
 an environment sensor section for detecting environmental data which is capable of affecting the blood vessel evaluation information;
 an event detection section which detects an occurrence point in time and type of event as an event which is capable of affecting the blood vessel evaluation information, when the environment data reaches a specific range;
 a threshold value storage section which stores a threshold value for specifying the specific range corresponding to a type of environmental data detected by the environment sensor section and a type of event; and
 an event storage section which stores the type and occurrence point in time of the event.

<u>Column 32,</u>
Line 31, please change Claim 20 to read:

20. The biological information evaluation apparatus according to claim 10, further comprising:
 a notification section that provides a notification of an analysis result in the change analysis section.

UNITED STATES PATENT AND TRADEMARK OFFICE
CERTIFICATE OF CORRECTION

PATENT NO. : 6,592,528 B2
DATED : July 15, 2003
INVENTOR(S) : Kazuhiko Amano

It is certified that error appears in the above-identified patent and that said Letters Patent is hereby corrected as shown below:

Column 32, cont'd.,
Line 35, please change Claim 21 to read:

21. A biological information evaluation apparatus comprising:
   a waveform parameter detection section which detects a specific waveform parameter based on a pulse waveform;
   a corresponding relation storage section which stores the corresponding relation between blood vessel evaluation information and a waveform parameter which is derived in advance of detection of the specific waveform parameter by the waveform parameter detection section;
   a blood vessel evaluation information deriving section which derives the blood vessel evaluation information based on the waveform parameter detected by the waveform parameter detection section and the corresponding relation;
   a blood vessel evaluation information storage section which stores the blood vessel evaluation information; and
   a basal blood vessel evaluation information deriving section which derives the blood vessel evaluation information when the basal metabolism of a subject is in a lowest region during a specific period of time based on the blood vessel evaluation information stored in the blood vessel evaluation information storage section.

Line 46, please change Claim 22 to read:

22. A biological information evaluation apparatus comprising:
   a waveform parameter detection section which detects a specific waveform parameter based on a pulse waveform;
   a corresponding relation storage section which stores the corresponding relation between blood vessel evaluation information and a waveform parameter which is derived in advance of detection of the specific waveform parameter by the waveform parameter detection section; and
   a blood vessel evaluation information deriving section which derives the blood vessel evaluation information based on the waveform parameter detected by the waveform parameter detection section and the corresponding relation; and
   wherein the blood vessel evaluation information is a physiological age of a blood vessel.

UNITED STATES PATENT AND TRADEMARK OFFICE
CERTIFICATE OF CORRECTION

PATENT NO.    : 6,592,528 B2
DATED         : July 15, 2003
INVENTOR(S)   : Kazuhiko Amano It is certified that error appears in the above-identified patent and that said Letters Patent is hereby corrected as shown below:

<u>Column 32, cont'd.,</u>
Line 59, please change Claim 24 to read:

24. The biological information evaluation apparatus according to claim 23, further comprising:
  a notification section that provides a notification of an analysis result in the comparative analysis section.

<u>Column 33,</u>
Line 17, please change Claim 26 to read:

26. A biological information evaluation apparatus comprising:
    a waveform parameter detection section which detects a specific waveform parameter based on a pulse waveform;
    a corresponding relation storage section which stores the corresponding relation between blood vessel evaluation information and a waveform parameter which is derived in advance of detection of the specific waveform parameter by the waveform parameter detection section;
    a blood vessel evaluation information deriving section which derives the blood vessel evaluation information based on the waveform parameter detected by the waveform parameter detection section and the corresponding relation;
    a data input section into which an actual age of a subject is input; and
    a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age; and
    wherein the blood vessel evaluation information is a degree of arteriosclerosis of a blood vessel.

UNITED STATES PATENT AND TRADEMARK OFFICE
CERTIFICATE OF CORRECTION

PATENT NO.   : 6,592,528 B2
DATED        : July 15, 2003
INVENTOR(S)  : Kazuhiko Amano It is certified that error appears in the above-identified patent and that said Letters Patent is hereby corrected as shown below:

Column 33,
Line 21, please change Claim 27 to read:

27. A biological information evaluation apparatus comprising:

a waveform parameter detection section which detects a specific waveform parameter based on a pulse waveform;

a corresponding relation storage section which stores the corresponding relation between blood vessel evaluation information and a waveform parameter which is derived in advance of detection of the specific waveform parameter by the waveform parameter detection section;

a blood vessel evaluation information deriving section which derives the blood vessel evaluation information based on the waveform parameter detected by the waveform parameter detection section and the corresponding relation;

a data input section into which a birth date of a subject is input;

an actual age calculation section which calculates an actual age of the subject based on the birth date of the subject input into the data input section; and a comparative analysis section which compares and analyzes the degree of arteriosclerosis of the blood vessel based on the degree of arteriosclerosis of the blood vessel derived by the blood vessel evaluation information deriving section and a standard degree of arteriosclerosis at the actual age, wherein the actual age calculation section comprises a birth date storage section which stores the birth date of the subject input into the data input section, and a present date calculation section which calculates a present date, and calculates the actual age of the subject based on the birth date of the subject stored in the birth date storage section and the present date calculated in the present date calculation section, and wherein the blood vessel evaluation information is a degree of arteriosclerosis of a blood vessel.

This certificate supersedes Certificate of Correction issued August 17, 2004 and November 23, 2004.

Signed and Sealed this

Twenty-fourth Day of May, 2005

JON W. DUDAS
*Director of the United States Patent and Trademark Office*